US010569028B2

(12) United States Patent
Bitton et al.

(10) Patent No.: US 10,569,028 B2
(45) Date of Patent: Feb. 25, 2020

(54) DRUG TRACKING DEVICE

(71) Applicant: INSULINE MEDICAL LTD., Petah Tikva (IL)

(72) Inventors: Gabriel Bitton, Jerusalem (IL); Gal Ben-David, Adi (IL)

(*) Notice: Subject to any disclaimer, the term of this patent is extended or adjusted under 35 U.S.C. 154(b) by 185 days.

(21) Appl. No.: 15/524,999

(22) PCT Filed: Nov. 5, 2015

(86) PCT No.: PCT/IL2015/051073
§ 371 (c)(1),
(2) Date: May 5, 2017

(87) PCT Pub. No.: WO2016/071912
PCT Pub. Date: May 12, 2016

(65) Prior Publication Data
US 2018/0280624 A1   Oct. 4, 2018

Related U.S. Application Data

(60) Provisional application No. 62/075,293, filed on Nov. 5, 2014.

(51) Int. Cl.
*A61M 5/32* (2006.01)
*A61M 5/315* (2006.01)
(Continued)

(52) U.S. Cl.
CPC ........ *A61M 5/3202* (2013.01); *A61M 5/3155* (2013.01); *A61M 5/31525* (2013.01);
(Continued)

(58) Field of Classification Search
CPC .. A61M 2205/3569; A61M 2205/3575; A61M 5/14244
See application file for complete search history.

(56) References Cited

U.S. PATENT DOCUMENTS 5,363,842 A * 11/1994 Mishelevich ........ A61B 8/0875
128/200.14
8,038,629 B2 * 10/2011 Solanki ................... A61B 7/04
128/200.24
(Continued)

FOREIGN PATENT DOCUMENTS

WO   WO 2008/114218 A2   9/2008
WO   WO 2010/052579 A2   5/2010
(Continued)

OTHER PUBLICATIONS

International Search Report and Written Opinion, dated Mar. 18, 2016, for International Application No. PCT/IL2015/051073.

*Primary Examiner* — Laura A Bouchelle

(57) ABSTRACT

A drug dispensing-tracking device configured in the form of at least one of a cover, a sleeve, and a cap, and configured to connect with a drug-injection or storage device. The tracking device may comprise at least one or more of: an acoustic sensor, a vibration sensor, an optical sensor, an optical-navigation sensor, and a magnetic sensor, and any combination thereof. At least one sensor may be configured to produce at least one respective signal in response to sensing a vibration, a sound, light, movement, and a magnetic field, respectively, produced by the drug-injection device due to an activity of the drug-injection device.

19 Claims, 28 Drawing Sheets

(51) Int. Cl.
  *G06F 19/00*  (2018.01)
  *G01F 11/02*  (2006.01)
  *G01B 11/02*  (2006.01)

(52) U.S. Cl.
  CPC ......... *G01F 11/023* (2013.01); *G01F 11/029* (2013.01); *G06F 19/3456* (2013.01); *A61M 2205/14* (2013.01); *A61M 2205/331* (2013.01); *A61M 2205/3306* (2013.01); *A61M 2205/3317* (2013.01); *A61M 2205/3368* (2013.01); *A61M 2205/3375* (2013.01); *A61M 2205/3379* (2013.01); *A61M 2205/50* (2013.01); *A61M 2205/52* (2013.01); *A61M 2205/581* (2013.01); *A61M 2205/582* (2013.01); *A61M 2205/584* (2013.01); *A61M 2205/6054* (2013.01); *A61M 2230/201* (2013.01); *G01B 11/022* (2013.01)

(56) References Cited

U.S. PATENT DOCUMENTS

| | | | |
|---|---|---|---|
| 9,067,022 B2* | 6/2015 | Baek | ..................... A61M 5/178 |
| 2009/0051560 A1 | 2/2009 | Manning et al. | |
| 2011/0295215 A1 | 12/2011 | Nielsen et al. | |
| 2013/0197445 A1* | 8/2013 | Schabbach | ......... A61B 5/14532 |
| | | | 604/189 |
| 2013/0236872 A1 | 9/2013 | Laurusonis et al. | |

FOREIGN PATENT DOCUMENTS

| | | |
|---|---|---|
| WO | WO 2012/153295 A2 | 11/2012 |
| WO | WO 2014/064691 A2 | 5/2014 |
| WO | WO 2014/152704 A1 | 9/2014 |

\* cited by examiner

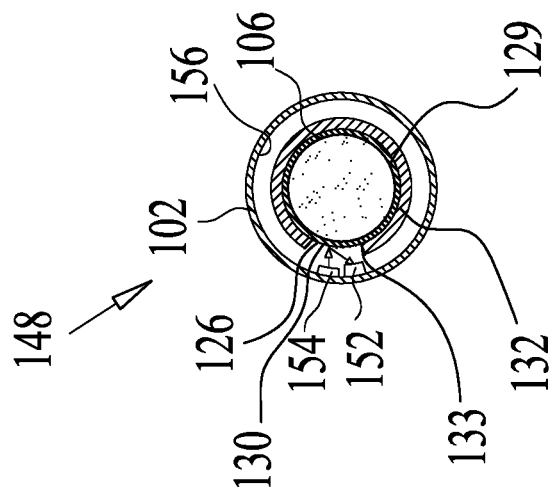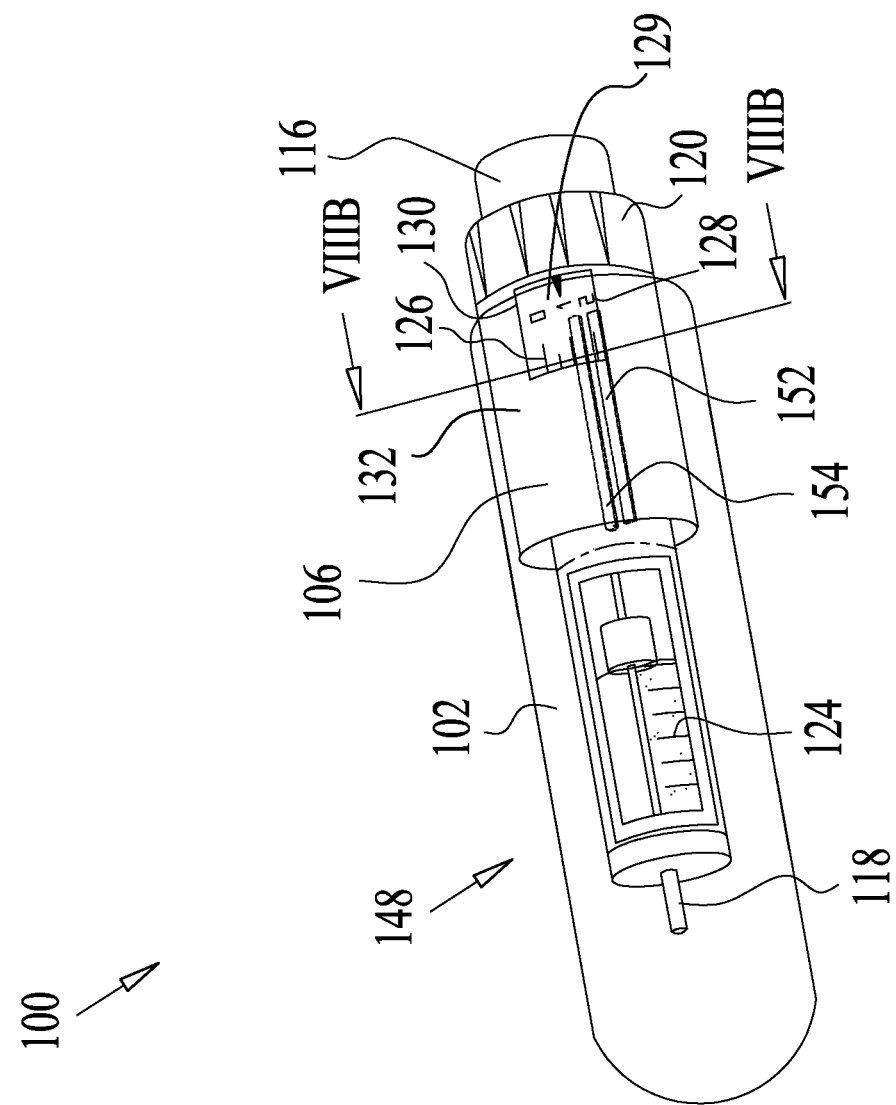

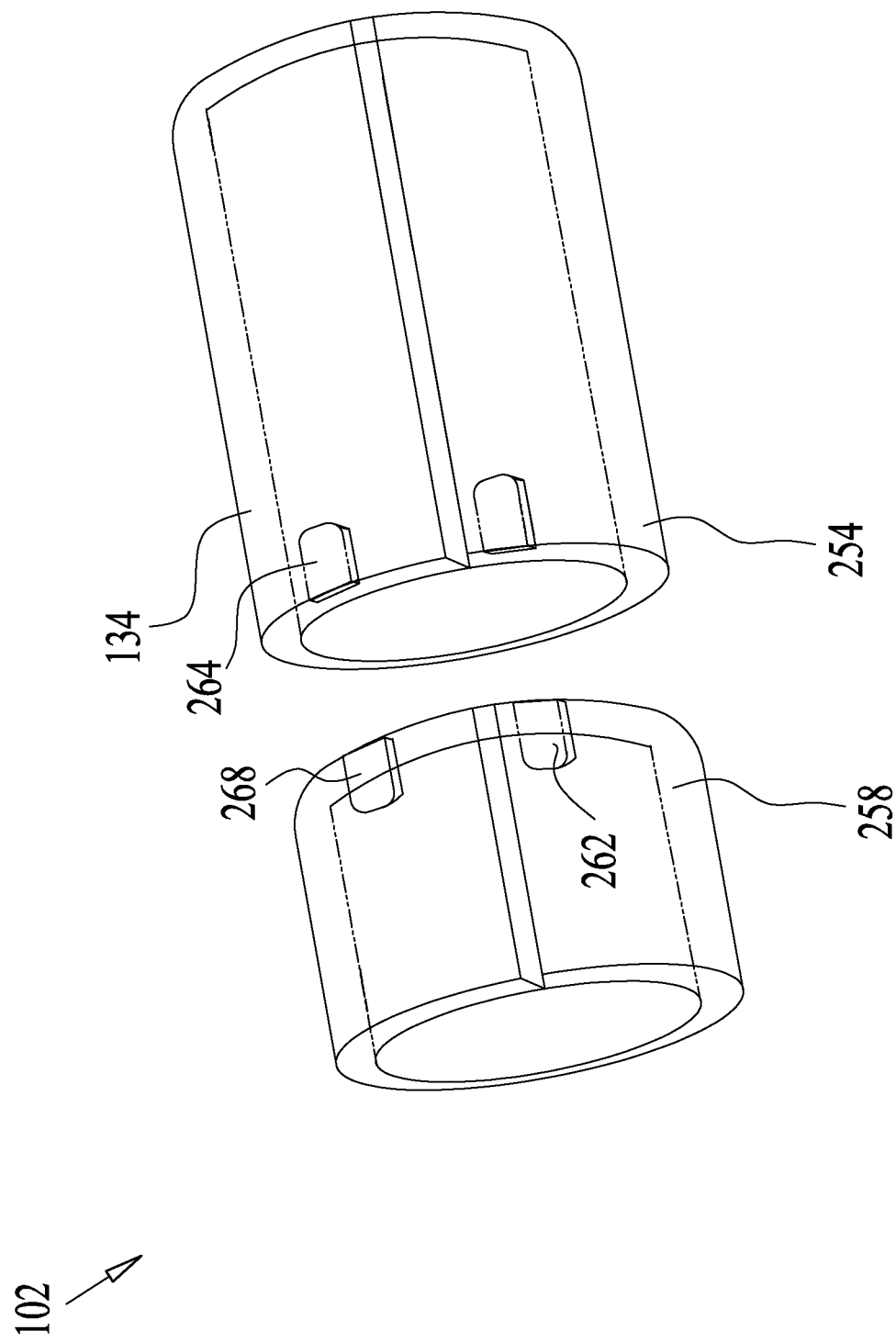

DRUG TRACKING DEVICE

CROSS REFERENCE TO RELATED APPLICATION

This application is a national stage entry of, and claims priority to, International Patent Application No. PCT/IL2015/051073, filed Nov. 5, 2015, entitled "Drug Tracking Device," which in turn claims priority to U.S. Provisional Patent Application No. 62/075,293, filed Nov. 5, 2014, entitled "Drug Dispensing-Tracking Device, System and Method" The present application incorporates herein by reference the disclosures of each of the above-referenced applications in their entireties.

TECHNICAL FIELD

Embodiments of the present disclosure generally relate to drug dispensers and tracking devices used to track the dispensed drug, as well as systems and corresponding methods thereof.

BACKGROUND

Various illnesses and disorders require multiple injections to control or treat a physiological condition. For example, insulin-dependent diabetics are required to inject several injections of insulin, of one or more types, each day to control their blood sugar levels. In order to track the treatment, some diabetics are required to log each injection in a log book and report the injections, as well as their blood sugar levels, at the time of injections to their physician on each visit to the physician. The data records may be used by the physician to administer further course of treatment. Therefore proper data recording is important to achieve improvement in treatment.

Patients, such as diabetics, during the course of their daily treatment, may use more than one injection device, disposable or reusable, to inject insulin, of the same or different type. Meanwhile, they usually use a single blood glucose meter to measure their blood glucose levels during that time. Therefore it is desirable to have a simple, inexpensive device and method which is capable of capturing and recording all injection events from one or more injection devices.

SUMMARY OF DISCLOSURE

In some embodiments of the present disclosure there is provided a drug dispensing-tracking device comprising a tracking device, configured in the form of at least one of a cover, a sleeve, and a cap, and configured to connect with a drug-injection or storage device. The tracking device may comprise at least one or more of: an acoustic sensor, a vibration sensor, an optical sensor, an optical-navigation sensor, and a magnetic sensor, and any combination thereof. At least one sensor may be configured to produce at least one respective signal in response to sensing a vibration, a sound, light, movement, and a magnetic field, respectively, produced by the drug-injection device due to an activity of the drug-injection device. The drug dispensing-tracking device may comprise a processor having operating thereon computer instructions for causing the processor to perform at least one of: receive, transmit, analyze and/or store information, at least a portion of the information may comprise at least one of: the at least one respective signal, a time corresponding to the at least one respective signal, an amount of drug injected by the drug-injection device, an amount of drug remaining in a reservoir associated with the drug-injection device following one or more drug injections, a duration since a previous injection; an age and/or expiration of the drug, a period of time since the manufacture of the drug, bio-potency/availability of the drug, a quality of the drug, a degree of cloudiness of the drug, a temperature of the drug, identification of the injection device, identification of the tracking device.

In some embodiments, the activity comprises setting or adjusting an amount of drug to inject, injecting the drug, and readying the drug-injection device. At least one sensor may comprise a plurality of sensors. The plurality of sensors may be arranged in an array. The plurality of sensors may be spaced apart along and/or around the tracking device.

In some embodiments, the acoustic sensor comprises a microphone and/or a vibration sensor for detecting a sound wave and/or vibration produced by the activity of the drug-injection device. The drug-injection device may comprise a pen-injection device wherein the amount of drug to be injected is set by rotating an injection-amount knob included with the injection device, wherein a series of clicking sounds and/or vibrations are produced by the rotation, each of which is sensed by the microphone and wherein the microphone produces at least one signal corresponding to the sensed sounds and/or vibrations.

In some embodiments, the drug-injection device comprises a pen-injection device having an injection push-button configured to initiate injection of the drug into a patient using injection dispensing means, wherein at least one of sound(s) and/or vibrations of at least one of the pushing of the button and the dispensing means is sensed by the microphone, and wherein the microphone produces at least one signal corresponding to the sensed sounds and/or vibrations.

In some embodiments, the sound of the rotation of the knob comprises a first sound for rotation of the knob in a first direction and a second sound in a second direction, and wherein the computer instructions are additionally configured to adjust one or more of the amount of drug injected by the drug-injection device, and/or an amount of drug remaining in a reservoir associated with the drug-injection device.

In some embodiments, the drug dispensing-tracking device may comprise a transceiver for at least one of transmitting and receiving information to/from a wireless device. The computer instructions may additionally be configured to cause the processor to transmit the information via the transceiver to a wireless device.

The tracking device may be configured as a cap to fit over the injection device. The cap may be configured such that the one or more sensors are arranged thereon to be proximate the knob and/or push-button when the cap is mounted on the injection device.

In some embodiments, the drug-injection device may include a shaft, and wherein the tracking device is configured as a sleeve and the sleeve is configured to be received onto the shaft. The sleeve is configured such that one or more sensors are arranged thereon to be proximate the knob and/or push-button when the sleeve is mounted on the injection device. At least a portion of the tracking device may include a coupling material configured to relay a sound(s) and/or vibration. At least a portion of the tracking device may include an isolating material configured to isolate sounds not generated by the injection device.

In some embodiments, the optical sensor may be selected from the group consisting of: a CCD, a CCD array, a photodiode, a waveguide, and/or a combination of any of the foregoing. The drug dispensing-tracking device may further include a light source, wherein the optical sensor is paired therewith. The drug dispensing-tracking device may further comprise one or more optical devices selected from the group consisting of one or more: lenses, light-guides, and beam splitters.

In some embodiments, at least one of the tracking device and drug-injection device includes scale markings configured to indicate at least one of an amount of drug in the reservoir and an amount of drug to inject. At least one of the tracking device and drug-injection device may include a window display configured for use with the scale markings.

A light source may be provided for use in combination with the optical sensor. The light source may be configured to illuminate the scale markings. The injection device may further comprise a reservoir with a transparent portion configured to provide an indication of an amount of drug contained therein for imaging by an optical sensor.

The drug dispensing-tracking device may further comprise a passive sensor configured to provide a physical property to indicate a change in the quality of the drug. The physical property may be a color, and wherein the optical sensor may be configured to image the passive sensor to monitor any change in color of the passive sensor. The color change may comprise a change in the degree of clarity or cloudiness of the drug.

In some embodiments, the information is transmitted to a second device, and the second device may be configured to be displayed via at least one of the second device and a third device. The computer instructions may be additionally configured to cause the processor to transmit the information via a transceiver or wireline connection to the second device. The second device may be configured to alert a user of the information.

In some embodiments, the optical sensor may be configured to detect exposure of the drug contained within the injection device to light. The optical sensor may be configured to detect exposure of the drug contained within the injection device to light of one or more predetermined wavelengths and/or intensity. The light exposure may correspond to a change in bio-potency of the drug contained in the drug-injection device. In some embodiments, the information corresponds to changes in the optical quality of the drug, wherein the optical quality of the drug corresponds to the bio-potency of the drug. In some embodiments, the computer instructions may be configured to cause the processor to transmit the information upon the bio-potency of the drug being at below a predetermined percentage.

In some embodiments, at least one of the optical sensor and optical navigation sensor is configured to sense at least one of a movement of a drug within the drug injection device, movement of a reservoir containing the drug, movement of a surface of the drug injection device, movement of a marking on the drug injection device, relative to at least one of the drug, markings, and the drug-injection device. The movement detection may include at least one of direction, rotation, velocity, and distance determination. The optical sensor may be configured to sense movement of one or more components of the drug-injection device.

In some embodiments, the markings may comprise color codes, at least one of which is displayed to indicate at least one of the amount of drug to be injected, a total amount of drug injected over a period of time, and an amount of drug remaining in a reservoir of the drug-injection device. At least one of the light source and optical sensor may be configured to provide and detect, respectively, modulated light.

In some embodiments, the drug dispensing-tracking device may further comprise at least one magnet, wherein the at least one magnet is positioned on at least one of the tracking device and drug-injection device, wherein the magnetic sensor is configured to operate by sensing the magnetic field of the at least one magnet and/or the relative strength thereof. The magnet may be an electromagnet. The magnetic sensor may be configured to sense at least one of: movement of a reservoir containing the drug, movement of a knob for controlling an injection amount, and movement of one and/or another component of the drug-injection device. The movement detection may include at least one of direction, rotation, velocity, and distance determination.

In some embodiments, the computer instructions may be additionally configured to cause the processor to receive a plurality of signals from a plurality of sensors. The computer instructions may additionally be configured to cause the processor to accurately determine the information and/or filter one or more of the signals.

In some embodiments, at least one of the tracking device and drug-injection device includes a speaker, and wherein the computer instructions are additionally configured to cause the processor to process the information and output a sound to inform a user or other person of at least one of: a time corresponding an injection, an amount of drug injected by the drug-injection device, an amount of drug remaining in a reservoir associated with the drug-injection device following one or more drug injections, a duration since a previous injection, an age and/or expiration of the drug, a period of time since the manufacture of the drug, a bio-potency/availability of the drug, a quality of the drug, a degree of cloudiness of the drug, a temperature of the drug, identification of the injection device, identification of the tracking device. The sound may be a voice.

In some embodiments of the present disclosure the information may be transmitted to an application operating on a mobile device, and wherein the application causes the mobile device to output a sound to inform a user or other person of at least one of: a time corresponding an injection, an amount of drug injected by the drug-injection device, an amount of drug remaining in a reservoir associated with the drug-injection device following one or more drug injections, a duration since a previous injection, an age and/or expiration of the drug, a period of time since the manufacture of the drug, a bio-potency/availability of the drug, a quality of the drug, a degree of cloudiness of the drug, a temperature of the drug, identification of the injection device, identification of the tracking device.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other embodiments, features, objections and advantages thereof will be even more clear with reference to the corresponding drawings for the subject application (a brief description of which is provided immediately below), and following detailed description.

BRIEF DESCRIPTION OF THE DRAWINGS

FIGS. 8A and 8B are a schematic illustration of an exemplary drug dispensing-tracking system (8A) and a cross sectional illustration of FIG. 8A along lines VIIIB-VIIIB (8B) according to some embodiments of the present disclosure;

FIG. 23 is a schematic illustration of the tracking device shown in FIGS. 22A-22C;

Figure 1:
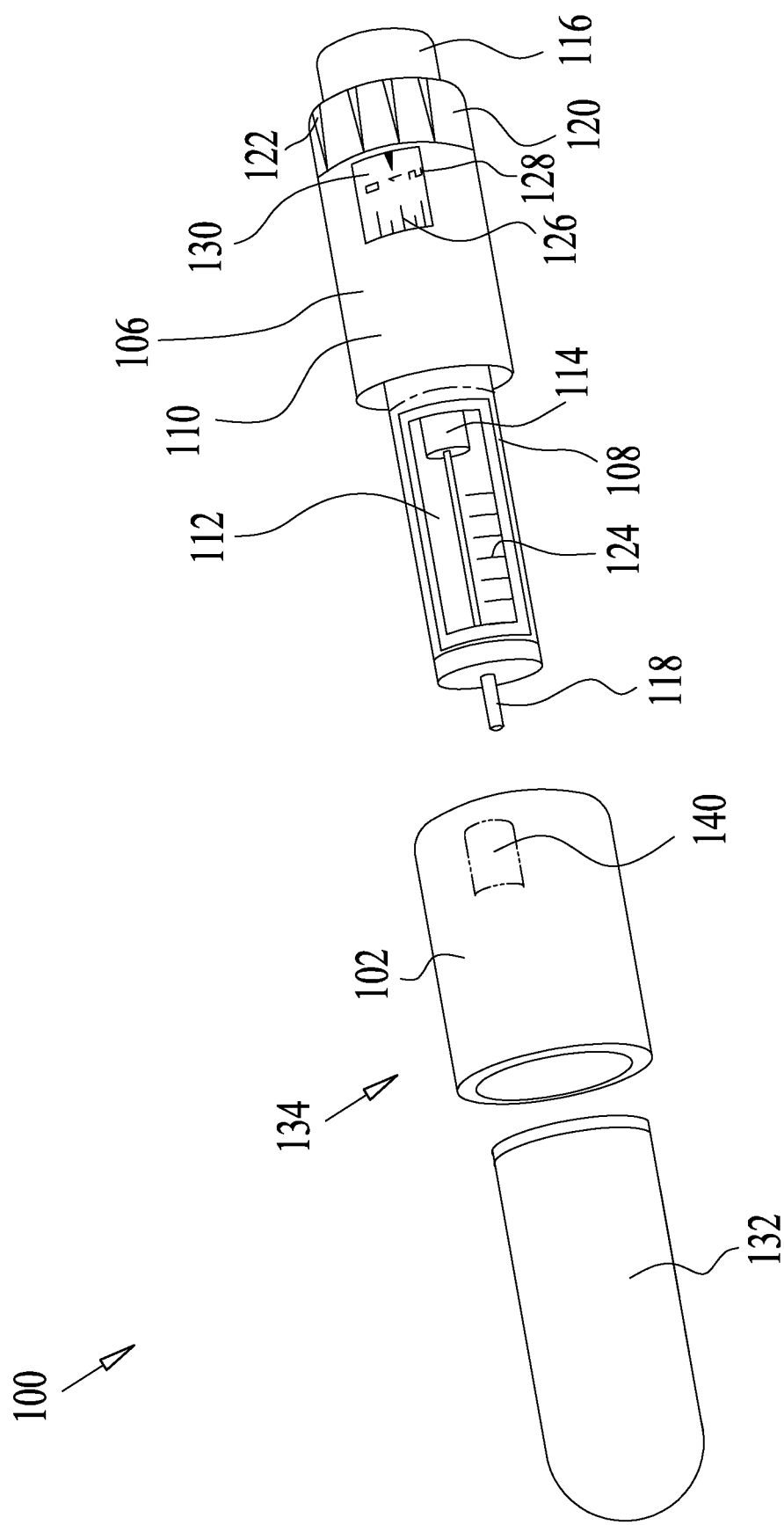
FIG. 1 is an exploded view of an exemplary drug dispensing-tracking system according to some embodiments of the present disclosure.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The principles and operations of the systems, apparatuses and methods according to some embodiments of the present disclosure may be better understood with reference to the drawings, and the following description. The drawings are given for illustrative purposes only and are not meant to be limiting.

DETAILED DESCRIPTION

FIGS. 1-5 are illustrations of an exemplary drug dispensing-tracking system 100 according to some embodiments of the present disclosure. The drug dispensing-tracking system 100 may comprise a tracking device 102 used in combination with a drug-injection or drug storage device 106.

Figure 18:
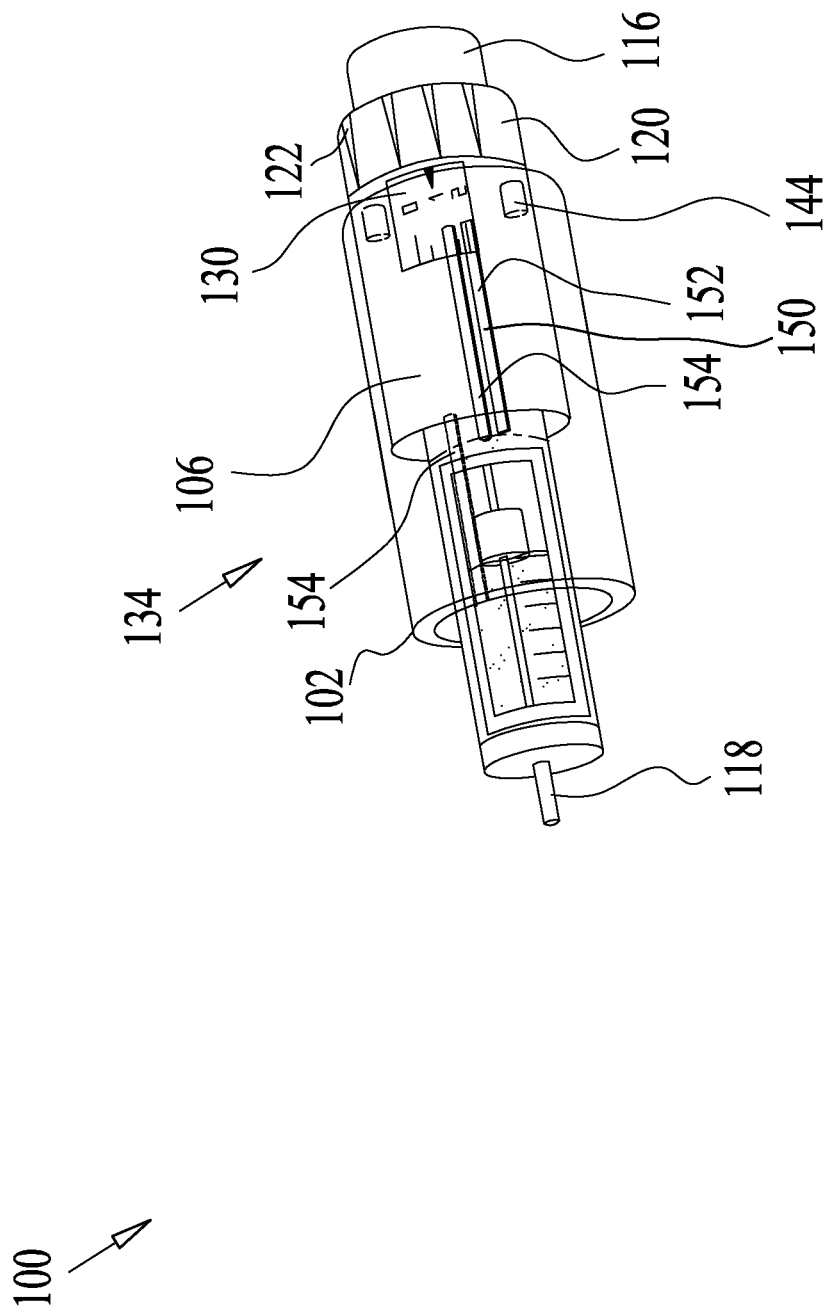
FIG. 18 is a schematic illustration of an exemplary drug dispensing-tracking system according to some embodiments of the present disclosure.
Figure 19:
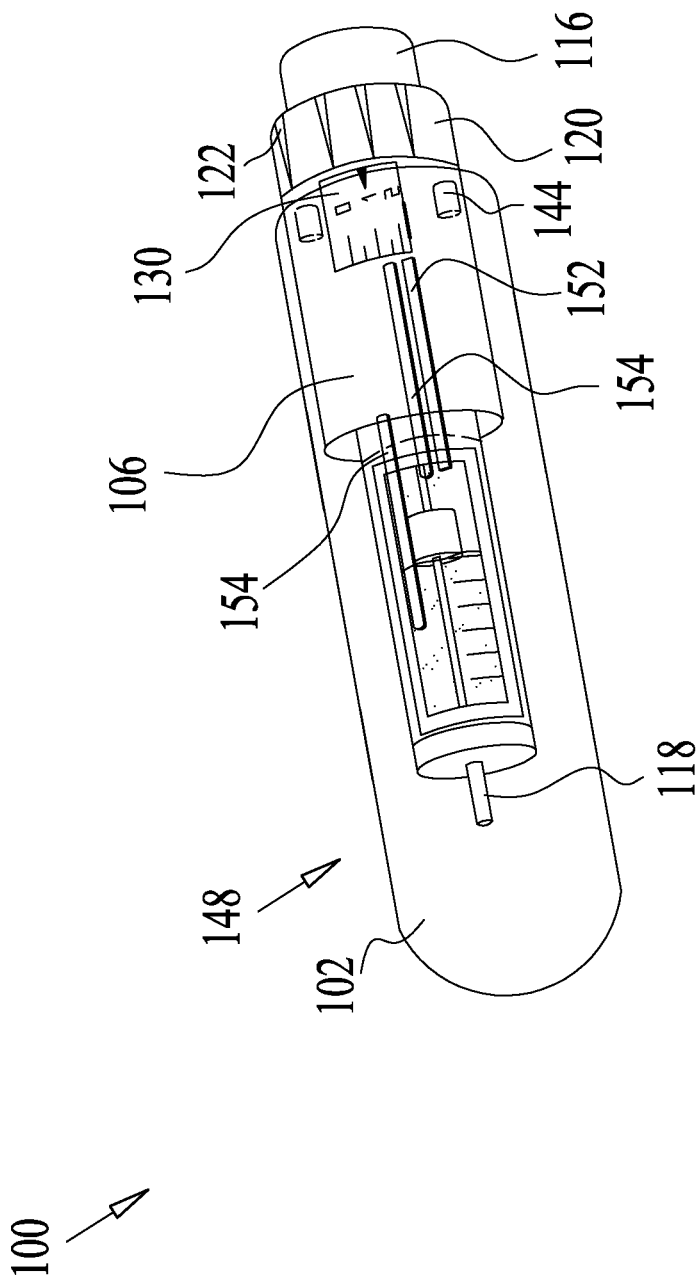
FIG. 19 is a schematic illustration of an exemplary drug dispensing-tracking system according to some embodiments of the present disclosure.
Figure 20:
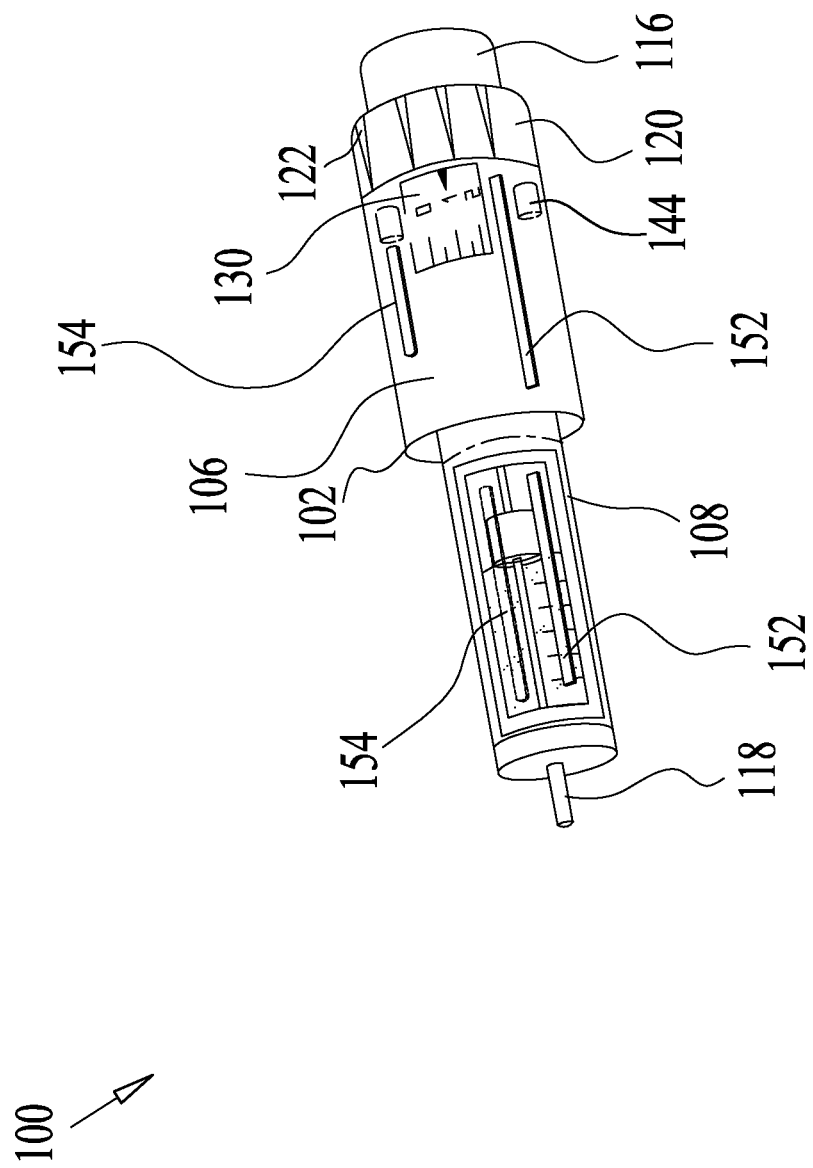
FIG. 20 is a schematic illustration of an exemplary drug dispensing-tracking system according to some embodiments of the present disclosure.

The tracking device 102 is configured for detecting activities related to the delivery of a drug. Exemplary tracking devices 102 may comprise an acoustic sensor 144 (FIGS. 2, 3 and 5), a vibration sensor 146 (FIG. 4), an optical sensor 150 (FIGS. 6-15), a magnetic sensor 170 (FIGS. 16 and 17) or a combination of two or more sensors (FIGS. 18-20).

The activities related to the delivery of a drug may comprise, inter alia, the injected dose of a drug; the amount of drug remaining in the injection device 106 following the drug injection; the time of injection; the time duration since the previous injection; the age of the drug, such as the time passed since the manufacturing of drug; the bioavailability of the drug; the optical quality of the drug; the degree of cloudiness of drug and the temperature of drug, as well as additional drug related data, such as described herein.

Figure 2:
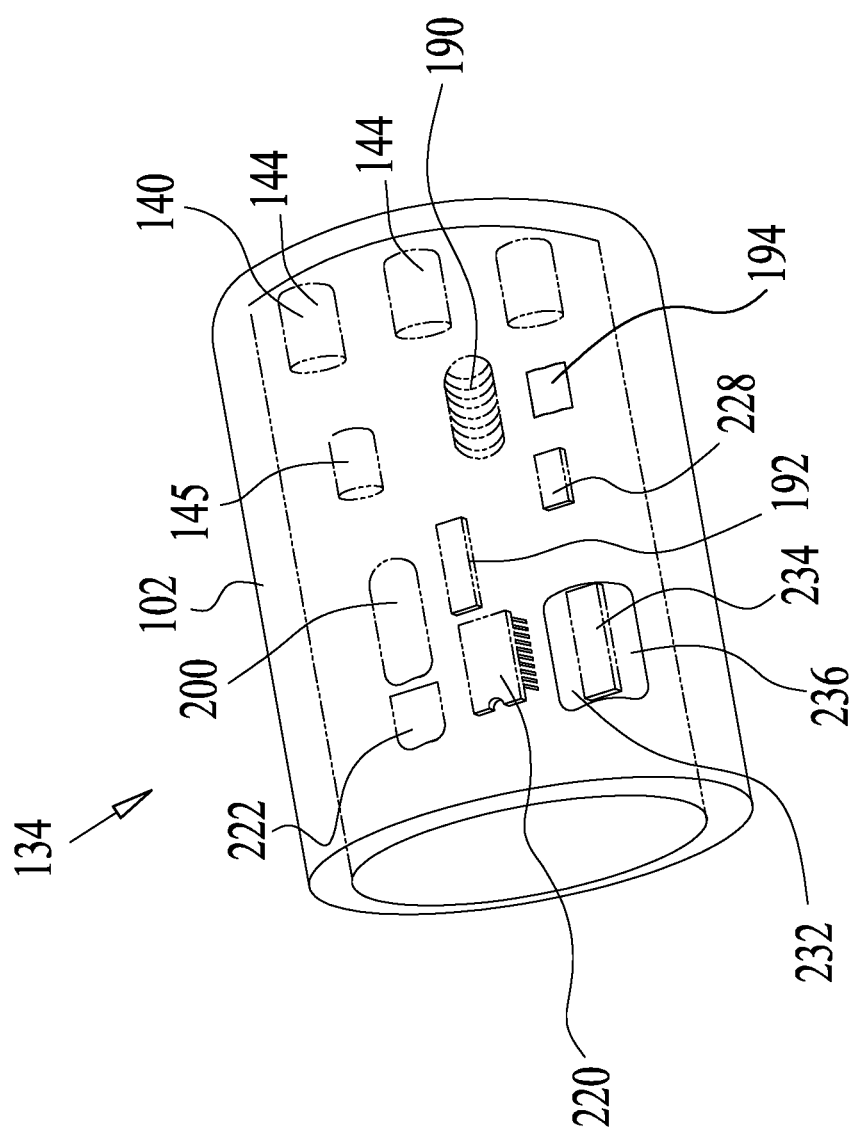
FIG. 2 is a schematic illustration of a tracking device shown in FIG. 1.
Figure 3:
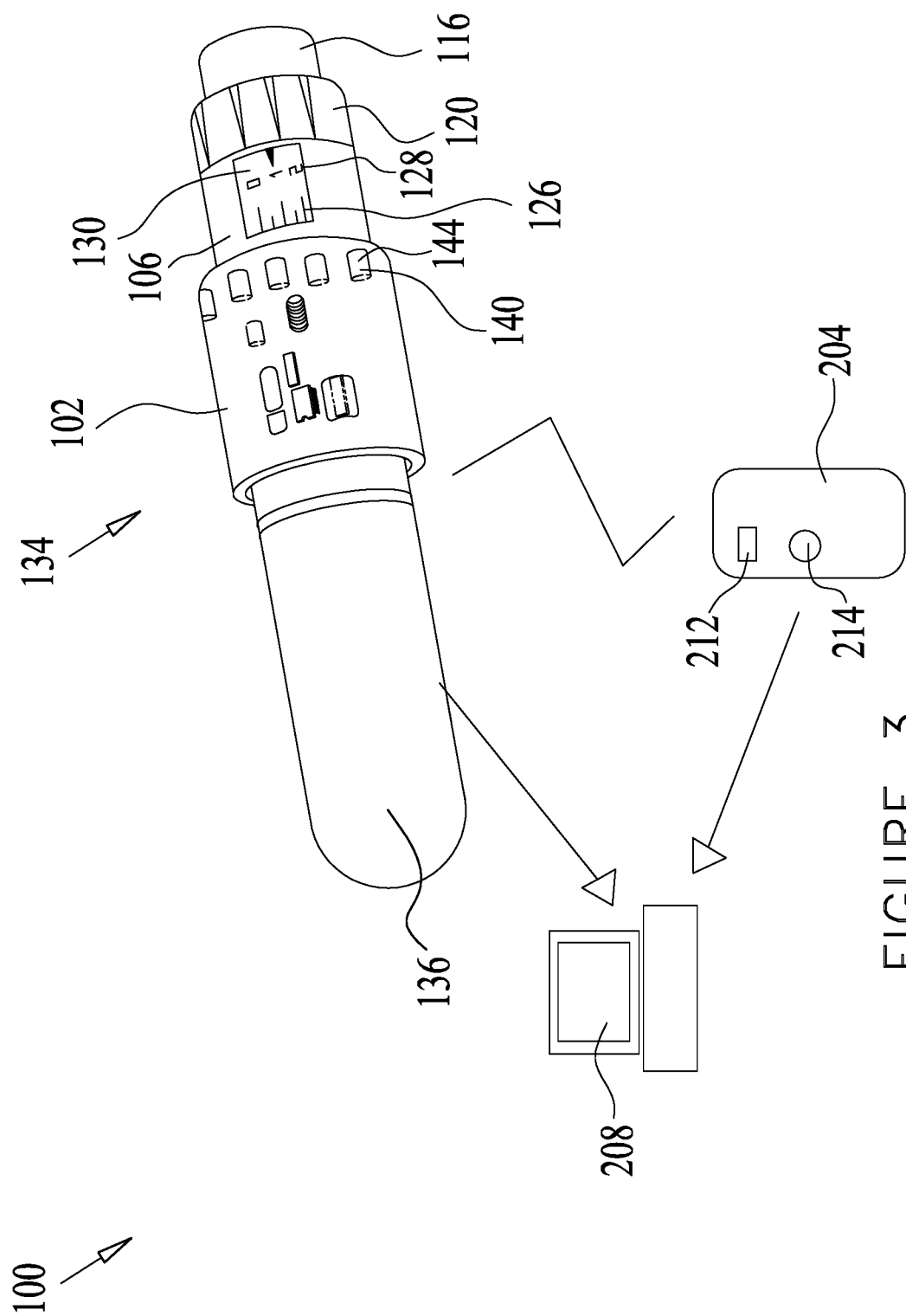
FIG. 3 is a schematic illustration of the assembled drug dispensing-tracking system shown in FIG. 1.

In some embodiments, the tracking device 102 may be formed as a sleeve, such as sleeve 134 of FIGS. 1-3. In some embodiments, the tracking device 102 may be formed as a cap, such as cap 148 of FIG. 4. In some embodiments, the tracking device 102 may be formed in the injection device, such as injection device 106 of FIG. 5.

As seen in FIG. 1, the injection device 106, configured for injection of a drug in a user, such as a patient, may comprise a shaft 108. The shaft 108 may be shaped in any suitable form, such as an elongated cylinder. The shaft 108 may comprise a first portion including a drug reservoir 110 containing a drug. The shaft 108 may comprise a second, generally transparent portion 112. Upon selection of a desired drug dose the drug is advanced from the drug reservoir 110 by a piston 114 into the shaft transparent portion 112. The drug may be injected by pressing a button 116 (e.g. a push-button) which urges dispensing of the drug from the shaft transparent portion 112 through a needle 118 into a patient.

Figure 26:
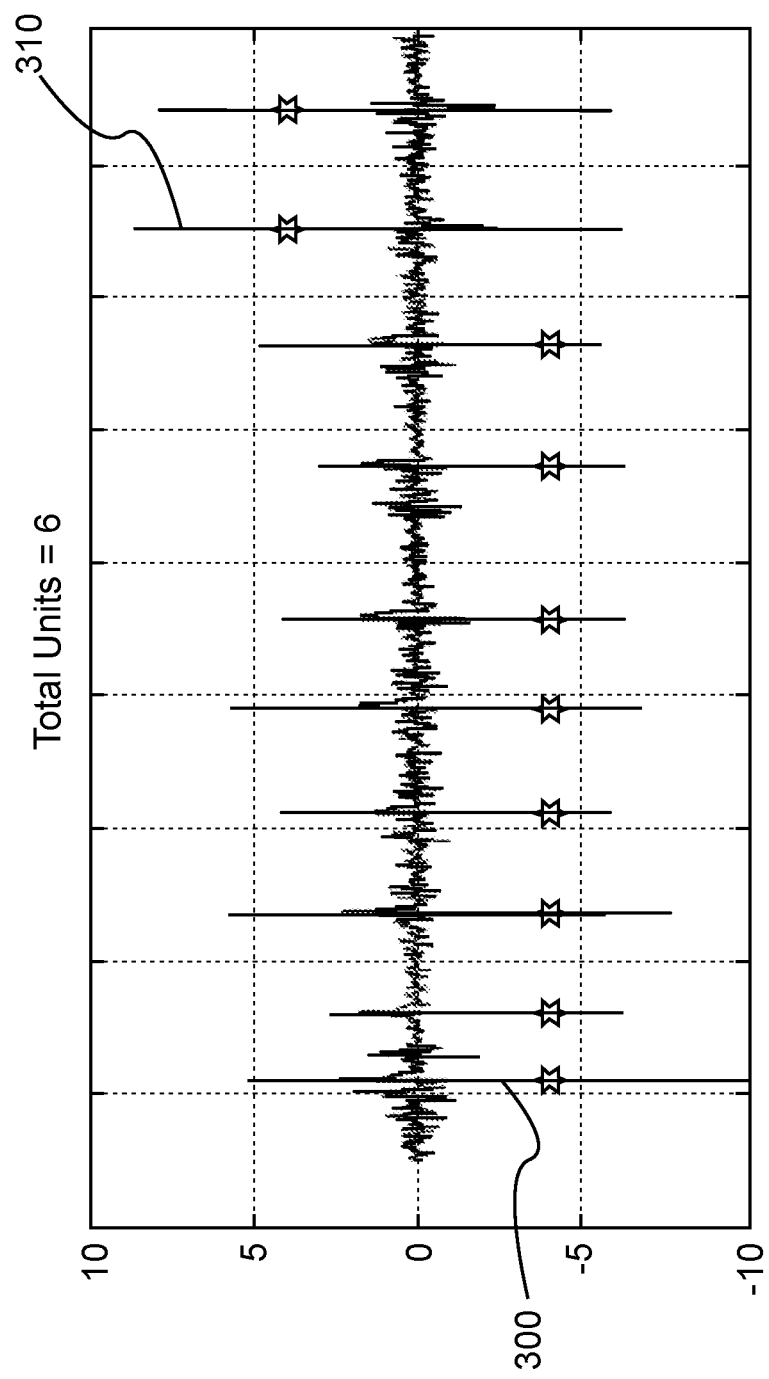
FIG. 26 is a graph illustrating a method for tracking dispensing of a drug from an injection device according to some embodiments of the present disclosure.

In some embodiments, a desired dose of injected drug may be determined by rotating a rotation knob 120. The rotation knob 120 may comprise a plurality of notches 122 or any other indicator. The rotation of the notch 122 to a first direction (e.g. clockwise) is performed to set the dose of drug to be dispensed from the drug reservoir 110, before the drug is injected. The rotation of the notch 122 to a second, opposite direction (e.g. counterclockwise) is performed to correct, if necessary, the dose of drug to be dispensed from the drug reservoir 110. Prior to injection, a patient may determine the desired dose of injected drug by the number of notches rotated. In some embodiments, the rotation of the knob 120 to the first or second direction may be accompanied by a clicking sound. These sounds (created by rotating the knob 120 to first or second directions) may be different when properly analyzed, as illustrated in FIG. 26.

The predetermined dose of the drug released by the rotation of a notch 122 may be different in different injection devices 106. In a non-limiting example, the released dose may be of a single unit, 2 or 3 units, or a half of a unit. When the drug is insulin, a single drug unit may comprise 0.01 milliliters, for example. Thus, the rotation of a notch 122 may be a single unit of 0.01 milliliters of insulin, two units (0.02 ml), three units (0.03 ml), or a half of a unit (0.005 ml).

The type of drug may be different in different injection devices 106. In a non-limiting example, during the treatment course of a diabetic patient, different types and/or quantities of insulin are administrated, such as a basal insulin dose and a bolus insulin dose. The different doses may be injected by different injection devices 106. Accordingly, a patient may routinely use more than one drug-injection device 106 during the course of his daily treatment.

In some embodiments, scale markings 124 may be formed on the shaft transparent portion 112 and are indicative of the drug dose selected by rotation of the knob 120. Alternatively or additionally, scale markings 126 and a numerical display 128 may be formed on the circumference of an inner cylinder 129 (FIG. 8B) of the shaft first portion 110. Scale markings 126 and numerical display 128 are indicative of the drug dose selected by rotation of the knob 120. The inner cylinder 129 rotates along with the rotation of the knob 120. Rotation of the knob 120 causes rotation of the scale markings 126 and numerals 128, which represent the selected dose, in a display window 130. An outer cylinder 132 of the shaft first portion 110 overlies the inner cylinder 129 and is formed with an aperture 133 exposing the display window 130.

A cap 136 may cover the shaft 108.

When rotating the knob or when injecting the drug, the inner cylinder 129 may move in at least two directions: it rotates in the orientation of a rotation axis 138, which is perpendicular to a longitudinal axis 139 (FIG. 10) of the injection device 106 and also may move along longitudinal axis 139 in a screw-like movement.

In some embodiments, the injection device 106 may comprise an injection pen. The injection pen may be disposable, configured for limited or even single use or may be configured for multiple uses and fitted to receive replacement cartridges or vials. The cartridges or vials may comprise the shaft 108 including the drug reservoir 110 and the transparent portion 112. In some embodiments, the injection device 106 may comprise a syringe, such as a reusable or disposable syringe. The syringe may comprise the shaft 108 including the drug reservoir 110 and the transparent portion 112. The button 116 in the syringe may comprise a flange which pushes the drug through needle 118 into a patient. In some embodiments the injection device 106 may include a drug storage device.

The tracking device 102 may comprise a sensor 140, or an array of sensors, of the same or different types or any combination of sensors, configured to detect a signal indicating an activity performed by the injection device 106 or activities related to the delivery of a drug.

In some embodiments, the signal may be an auditory signal generated by an activity performed by the injection device 106. The sensor 140 may comprise an acoustic sensor 144, such as a microphone (FIG. 2), for detecting the auditory signal (i.e. a sound wave), such as the clicking sound generated by the rotation of the knob 120 and/or the pressing of the button 116. In some embodiments, auditory signals may include any vibration generated by setting and/or using the injection device. The microphone 144 may comprise any suitable configuration, such as an analog device including a low noise microphone, such as the ADMP504 or ADMP521 component or a device including a ADMP441-I2S component. In some embodiments, the number of clicks detected by the microphone 144 may indicate the dose of drug injected by the user. Additionally, the microphone 144 may detect different distinguishable sounds indicating the direction of the rotation of the knob 120, which as described, may correspond to addition or removal of the drug for injection thereof.

In some embodiments, such as when the sensor 140 comprises a microphone 144, the tracking device 102 may comprise an antenna 145 provided for wirelessly transmitting the signal.

In some embodiments, a plurality of microphones 144 may be provided and may be arranged around a periphery of the sleeve 134, as shown in FIG. 2, or may be arranged at any other location.

In some embodiments, the signal may be a vibration signal generated by an activity performed by the injection device 106. The sensor 140 may comprise a vibration sensor 146 (FIG. 4) for detecting the vibrations caused by the activity of the injection device 106, such as the rotation of the knob 120 and/or the pressing of the button 116. In some embodiments, the number of clicks detected by the vibration sensor may indicate the dose of drug injected by the user. Additionally, the vibration sensor 146 may detect the direction of the rotation of the knob 120, which as described, may correspond to addition or removal of the drug for injection thereof. Use of a vibration sensor 146 may be advantageous since it is unaffected by surrounding, ambient noises. The vibration sensor may be an accelerometer comprising, for example, piezoelectric, piezoresistive and/or capacitive components and/or may include a MEMS (micro electro-mechanical system) device, for example.

The acoustic sensor 144 or the vibration sensor 146 may be positioned in proximity to the knob 120. As seen in FIGS. 1-3, the sleeve 134 comprises the tracking device 102. The sleeve 134 is configured to be inserted on the shaft 108 and the acoustic sensor 144 or the vibration sensor 146 are positioned in proximity to the knob 120, as seen in FIG. 3.

Figure 4:
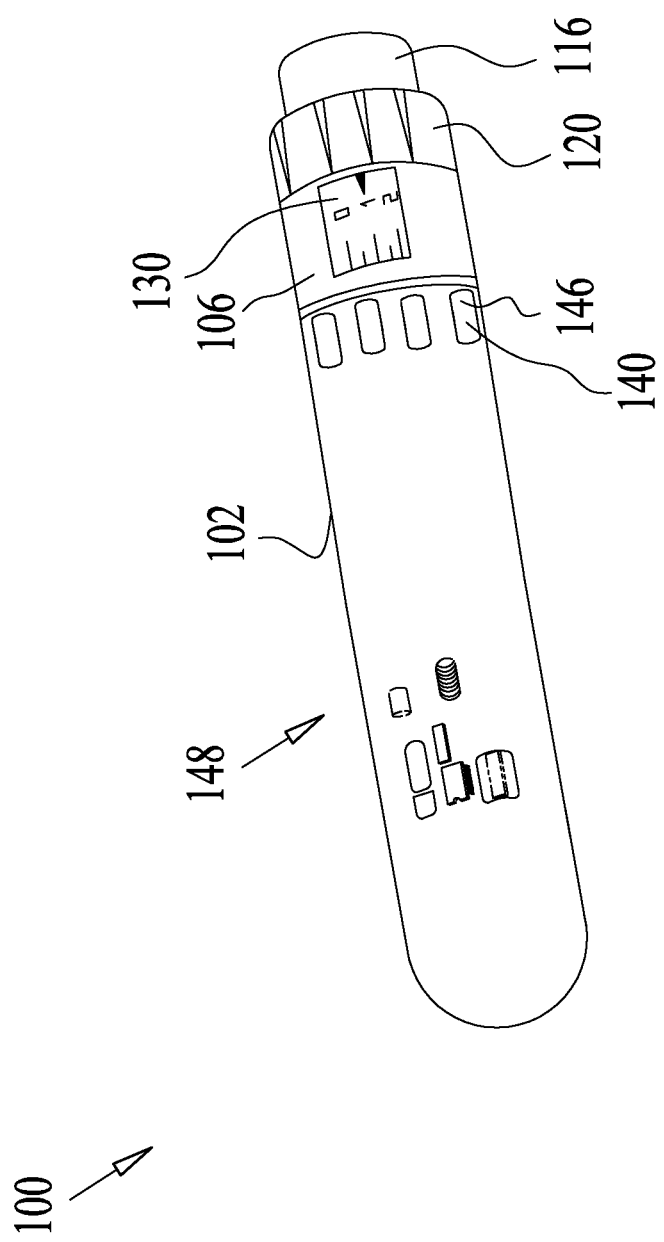
FIG. 4 is a schematic illustration of an exemplary drug dispensing-tracking system according to some embodiments of the present disclosure.

In some embodiments, the tracking device 102 may be formed as a cap 148 configured to be inserted on the shaft 108, as seen in FIG. 4. The cap 148 may be formed to replace a standard cap 136 of the injection device 106. The cap may be placed in proximity to the knob 120 so as to capture the rotation of the knob 120 by the acoustic sensor 144 or the vibration sensor 146. This may be performed by sizing the cap 148 to cover the shaft 108 such that the acoustic sensor 144 or the vibration sensor 146 is positioned in proximity to the knob 120. Setting the desired dose may be performed while the cap 148 is placed on the injection device 106. In another embodiment, the cap 148 may be removed, yet placed alongside the knob 120 to capture the acoustic or vibration signal.

Figure 5:
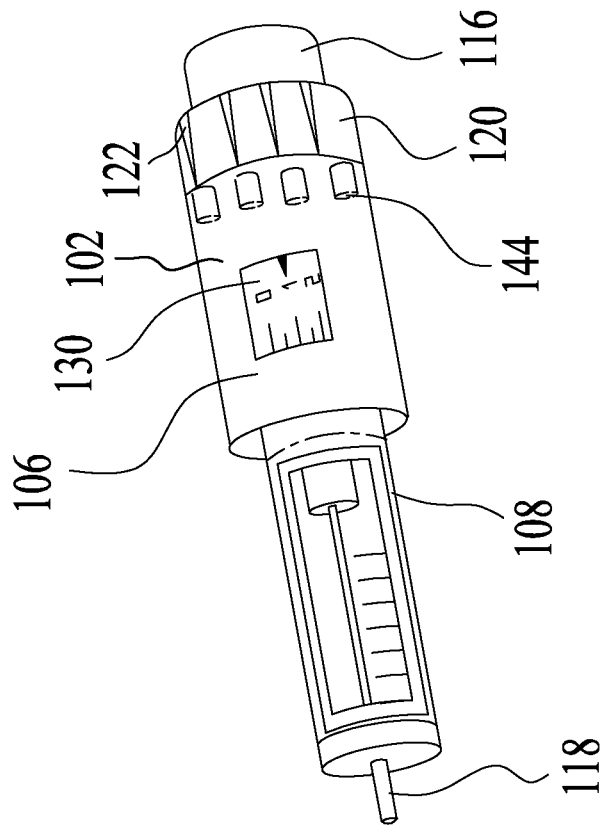
FIG. 5 is a schematic illustration of an exemplary drug dispensing-tracking system according to some embodiments of the present disclosure.

In some embodiments, the tracking device 102 may be formed as part of the injection device 106, as seen in FIG. 5. The acoustic sensors 144 or the vibration sensors 146 may be positioned in proximity to the knob 120 so as to capture a signal associated with rotation of the knob. In some embodiments, the tracking device 102 may be embedded in a cover forming the injection device 106.

In some embodiments, the tracking device 102 may comprise a coupling material provided to efficiently couple and transform the signal, such as the auditory signal or vibration signal, from the injection device 106 to the tracking device 102. The coupling material may comprise a sound conducting material, for example. A sound conducting material may comprise a material providing low attenuation and good coupling with the sound or vibration signal, such as a plastic, e.g. a thermoplastic, such as acrylonitrile butadiene styrene (ABS).

In some embodiments, the tracking device 102 may include an isolating material to isolate noises and other sound sources external to the injection device 106.

FIGS. 6-15 are schematic illustrations of an exemplary drug dispensing-tracking system according to some embodiments of the present disclosure. As seen in FIGS. 6-15, the signal may be an optical signal generated by an activity performed by the injection device 106. For example, the optical signal may be indicative of the selected drug dose and indicative of an injection event.

As seen in FIGS. 6-9, the sensor 140 may comprise an optical sensor 150, such as a CCD, a CCD array 152, a photodiode, a waveguide or any other means for imaging. In some embodiments, the optical sensor 150 may be paired with a light source 154, such as an array of LEDs and/or may be paired with optical devices, such as lenses, beam splitters, and further optical devices for detecting a drug related activity.

Figure 6:
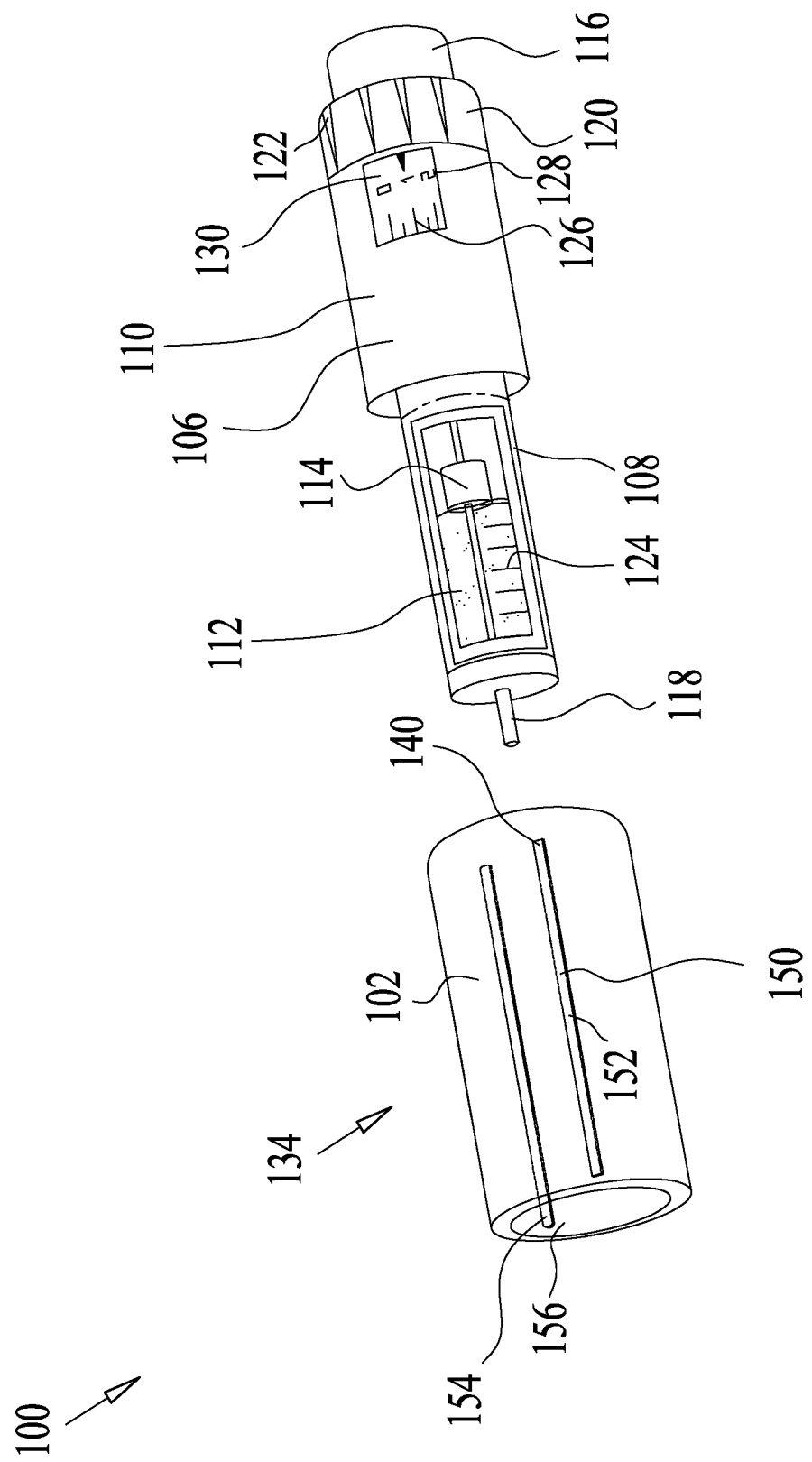
FIG. 6 is a schematic illustration of an exemplary drug dispensing-tracking system according to some embodiments of the present disclosure, in a disassembled state.
Figures 7A, 7B:
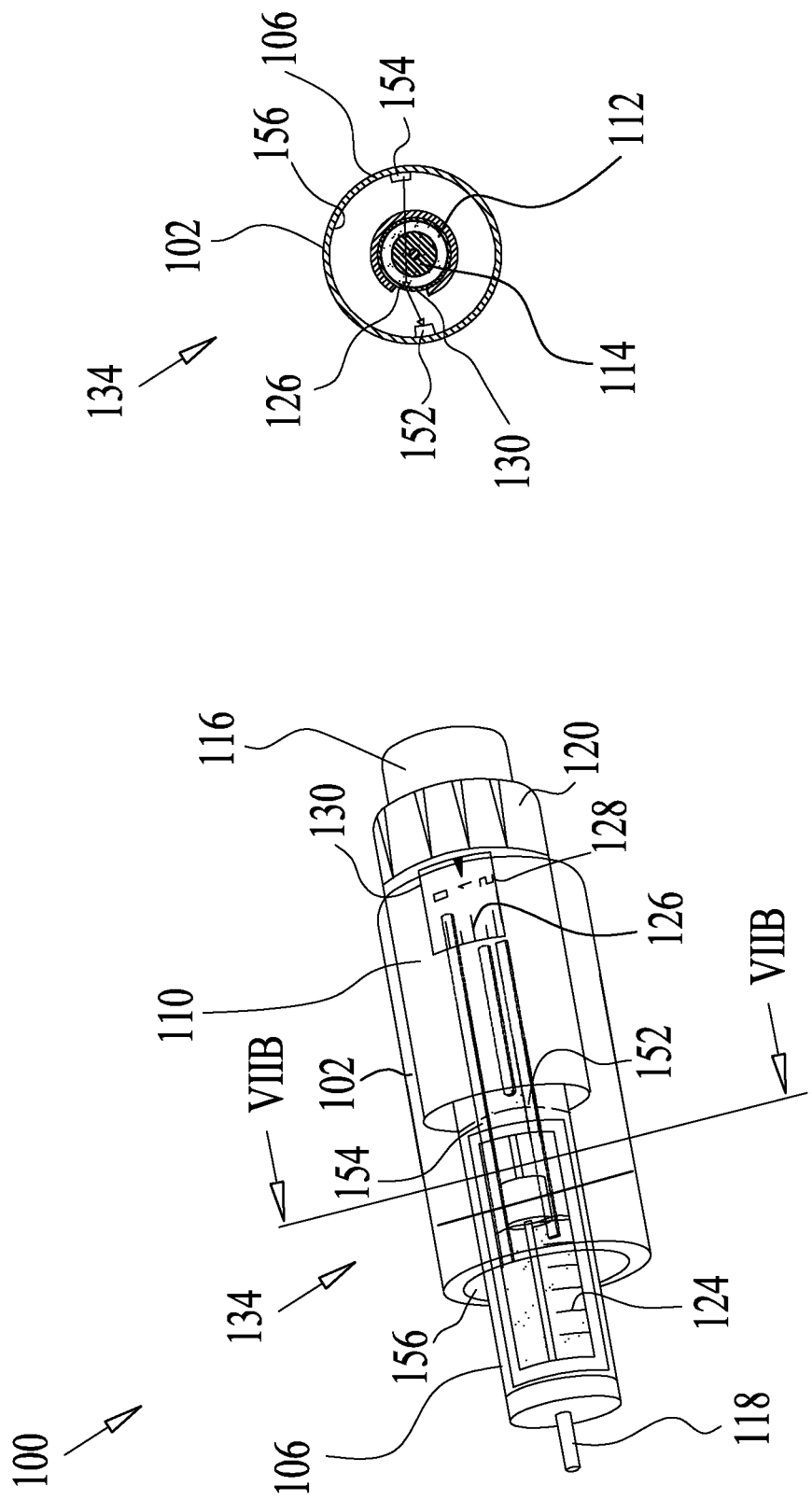
FIGS. 7A and 7B are a schematic illustration of the exemplary drug dispensing-tracking system of FIG. 6, in an assembled state (7A) and a cross sectional illustration of FIG. 7A along lines VIIB-VIIB (7B)
Figure 9:
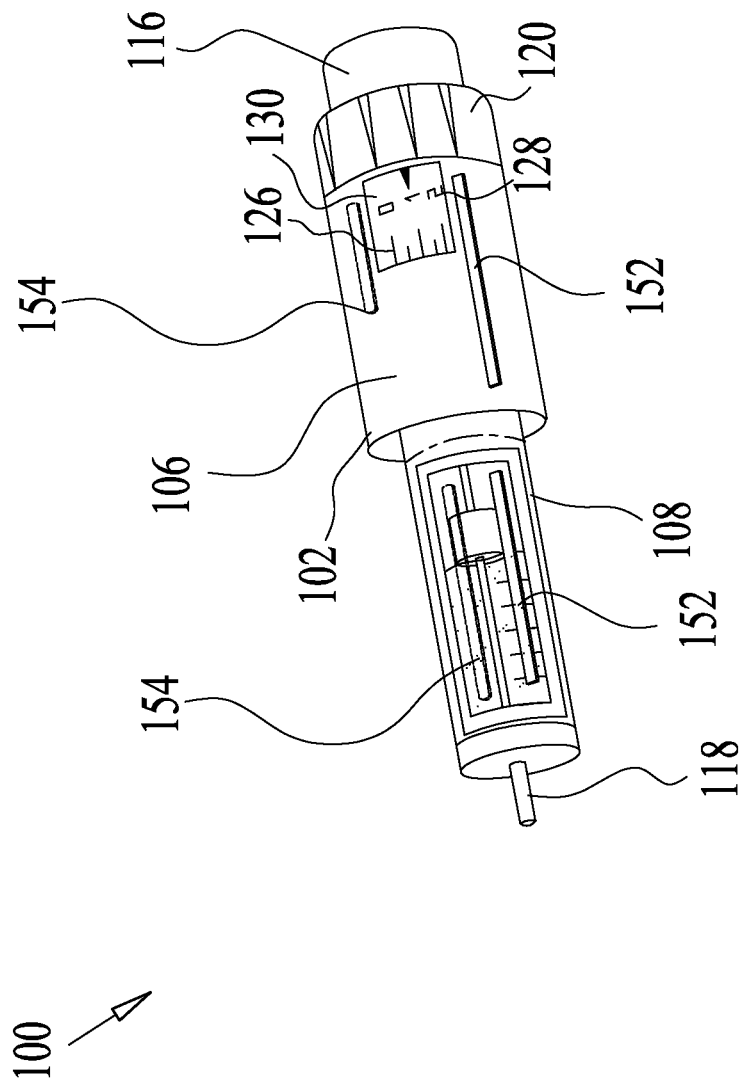
FIG. 9 is a schematic illustration of an exemplary drug dispensing-tracking system according to some embodiments of the present disclosure.

The optical sensor 150 and light source 154 of the tracking device 102 may be formed as a sleeve 134, as seen in FIGS. 6-7B. In some embodiments, the tracking device 102 may be formed as a cap 148, as seen in FIGS. 8A and 8B. In some embodiments, the tracking device 102 may be formed as part of the injection device 106, as seen in FIG. 9.

In some embodiments, the selected drug dose may be detected by imaging the scale marking 124 on the shaft transparent portion 112. The CCD array 152 and/or the light source 154 may be positioned at an inner surface 156 of the tracking device 102, for facing the scale markings 124 and window display 130.

In some embodiments, the light source 154 may be positioned at the same side as the optical sensor 150, to illuminate the scale marking 124, as shown for example in FIGS. 8A and 8B showing light source 154 placed alongside CCD array 152. The CCD array 152 images the scale marking 124 or 126 or numerals 128. In some embodiments, the light source 154 may be positioned opposite the CCD array surface to transmit light through the shaft transparent portion 112, as shown in FIGS. 7A and 7B. In FIG. 9, the tracking device 102 is shown to comprise a light source 154 placed opposite the CCD array as well as another light source 154 placed alongside the CCD array 152.

In some embodiments, the longitudinal length of the shaft transparent portion 112 containing the drug may be imaged by the optical sensor 150. In an injection device 106 where the total longitudinal length is known and the original number of drug units in the injection device 106 is known, the selected drug dose may be calculated.

In a non-limiting example, for an insulin injection device 106 with a longitudinal length of 4 cm, containing 300 insulin units, the CCD array 152 may image the transparent portion 112. Based on the image of the length of the filled transparent portion 112, the selected drug dose may be calculated and recorded. In some embodiments, the light source 154 may be positioned at the same side as the CCD array 150 to reflect the light on the drug filling the transparent portion 112. In some embodiments, the light source 154 may be positioned opposite the CCD array surface to transmit light through the empty shaft transparent portion 112. The drug dose can be calculated by deducting the imaged empty length from a total length of the transparent portion 112. The original, full amount of drug in the injection device 106 and/or the length of the injection device 106 may be recorded by the user or may be derived from the barcode or brand name of the injection device 106 or by any other suitable means.

Similar to detecting the selected drug dose prior to injection thereof, in some embodiments, the amount of drug remaining in the injection device 106 following injection, may be detected according to the methods described herein. Based on the image of the length of the empty transparent portion 112 or the length of the transparent portion 112 still containing the drug, the injected drug dose may be calculated and recorded.

In some embodiments, the selected drug dose may be detected by imaging the piston 114. The degree of displacement of the piston 114 along the longitudinal length of the injection device 106 may be indicative of the dose of selected drug or of the injected drug.

In some embodiments, the selected drug dose may be detected by imaging the scale markings 126 and numerals 128 in the display window 130. In some embodiments, the light source 154 may be positioned at the same side as the CCD array 152 to illuminate the display window 130.

In some embodiments, the optical sensor 150 may be a passive sensor which is configured to change a property thereof (e.g. color) to indicate a change in the optical quality of the drug. In some embodiments, the CCD array 152 may be used to image the optical quality of the drug. The optical quality of the drug may include the degree of clarity or cloudiness of the drug which may be indicative of the bioavailability of the drug. For example, some insulin drugs may have reduced bio-potency upon cloudiness of the drug.

In some embodiments, the user may be alerted upon detection of changes in the optical quality of the drug. Data indicative of the optical quality may be provided to the user, in any suitable manner, such as on the display 130 or via an external unit 204 and/or a central database 208 (FIG. 3), as will be further described. The bio-potency of the drug may be affected by changes in the optical quality of the drug. In some embodiments, the detected change of the optical quality of the drug may prompt the user to be alerted and informed of the degree of the current bio-potency of the drug. For example, an alert may inform the user that the bio-potency of the drug has been reduced to 95%, or to 90%, or to 85%, and lower. In some embodiments, upon reaching a predetermined bio-potency threshold the user may be alerted that the drug bio-potency has significantly diminished. In a non-limiting example, the bio-potency threshold may be a reduction in the range of about 5-10% from a fully potent drug. In a non-limiting example, the bio-potency threshold may be a reduction in the range of about 10-15% from a fully potent drug. In a non-limiting example, the bio-potency threshold may be a reduction in the range of about 15-20% from a fully potent drug. In a non-limiting example, the bio-potency threshold may be a reduction in the range of about 20-50% from a fully potent drug. The alert may be generated in any suitable form, such as a textual message shown in display 130, and/or a textual or verbal message provided by the external unit 204. The external unit 204 may be any wireless device: a router, a cell/mobile/smart phone, a cell/mobile tower, or any computer having wireless communication functionality. The external unit 204 can also be a glucose sensor or another device configured to operate with the tracking device 102.

In some embodiments, the sensor 140 may comprise an optical sensor formed in any suitable manner or any other sensor configured to detect the exposure of the drug to light. In a non-limiting example, the optical sensor may be a passive sensor which is configured to change a property thereof (e.g. color) to indicate a change in degree of exposure of the drug to an illumination wavelength or light intensity. The optical sensor may also be a photographic imager.

In some embodiments, the user may be alerted upon detection of changes in the degree of exposure to light intensity or to an illumination wavelength by the drug. These properties may be provided to the user, in any suitable manner, such as on the display 130 or via the external unit 204 and/or the central database 208. The bio-potency of the drug may be affected by changes in exposure degree to light intensity or to illumination wavelength, as well as the time duration of the exposure. In some embodiments, the detected change of these properties may prompt the user to be alerted and informed of the degree of the current bio-potency of the drug. For example, an alert may inform the user that the bio-potency of the drug has been reduced to 95%, or to 90%, or to 85%, and lower. In some embodiments upon reaching a predetermined bio-potency threshold the user may be alerted that the drug bio-potency has significantly diminished. In a non-limiting example, the bio-potency threshold may be a reduction in the range of about 5-10% from a fully potent drug. In a non-limiting example, the bio-potency threshold may be a reduction in the range of about 10-15% from a fully potent drug. In a non-limiting example, the bio-potency threshold may be a reduction in the range of about 15-20% from a fully potent drug. In a non-limiting example, the bio-potency threshold may be a reduction in the range of about 20-50% from a fully potent drug. The alert may be generated in any suitable form, such as a textual message shown in display 130, and/or a textual or verbal message provided by the external unit 204 and/or central database 208.

Figure 10:
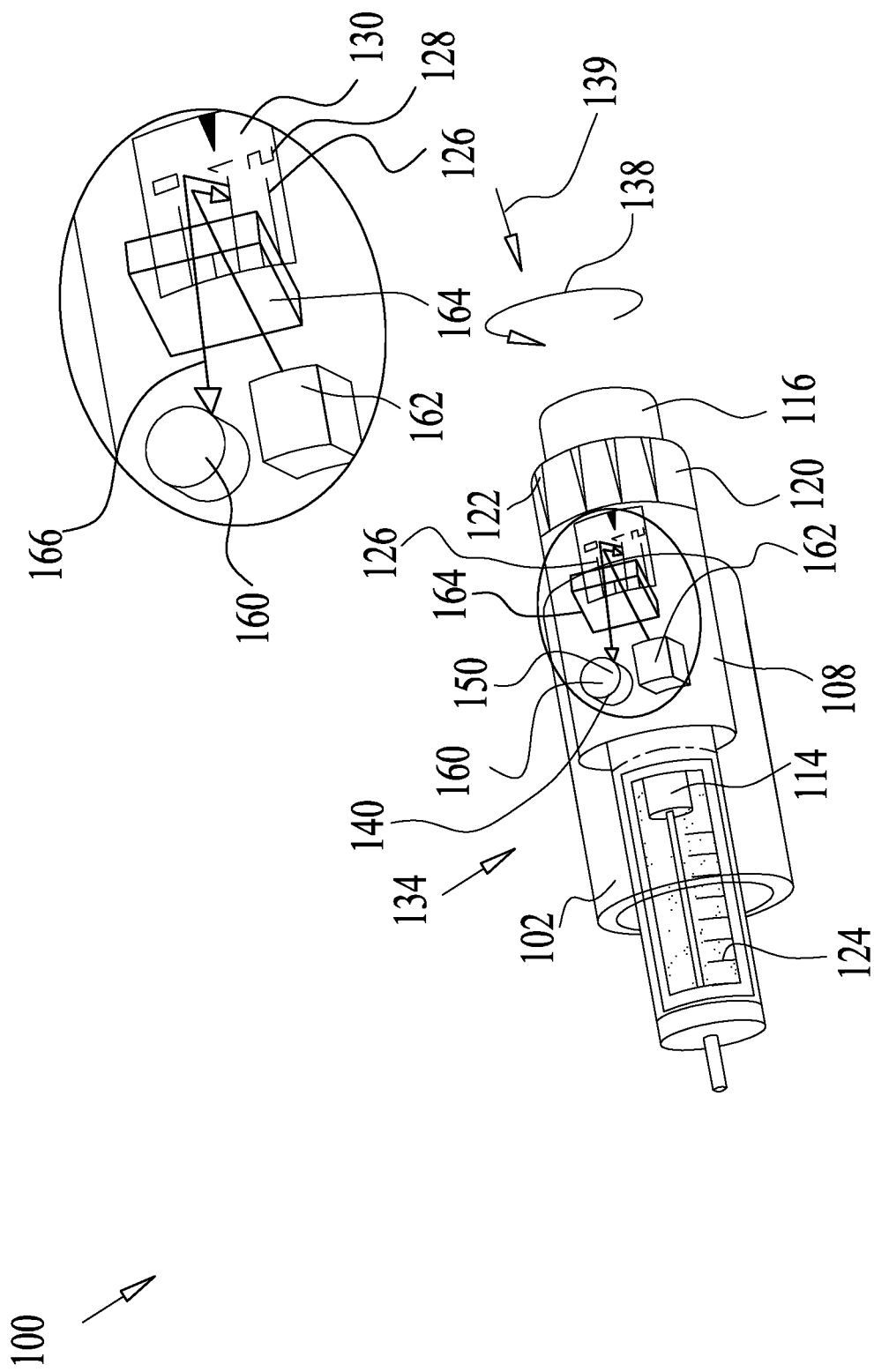
FIG. 10 is a schematic illustration of an exemplary drug dispensing-tracking system according to some embodiments of the present disclosure.
Figure 11:
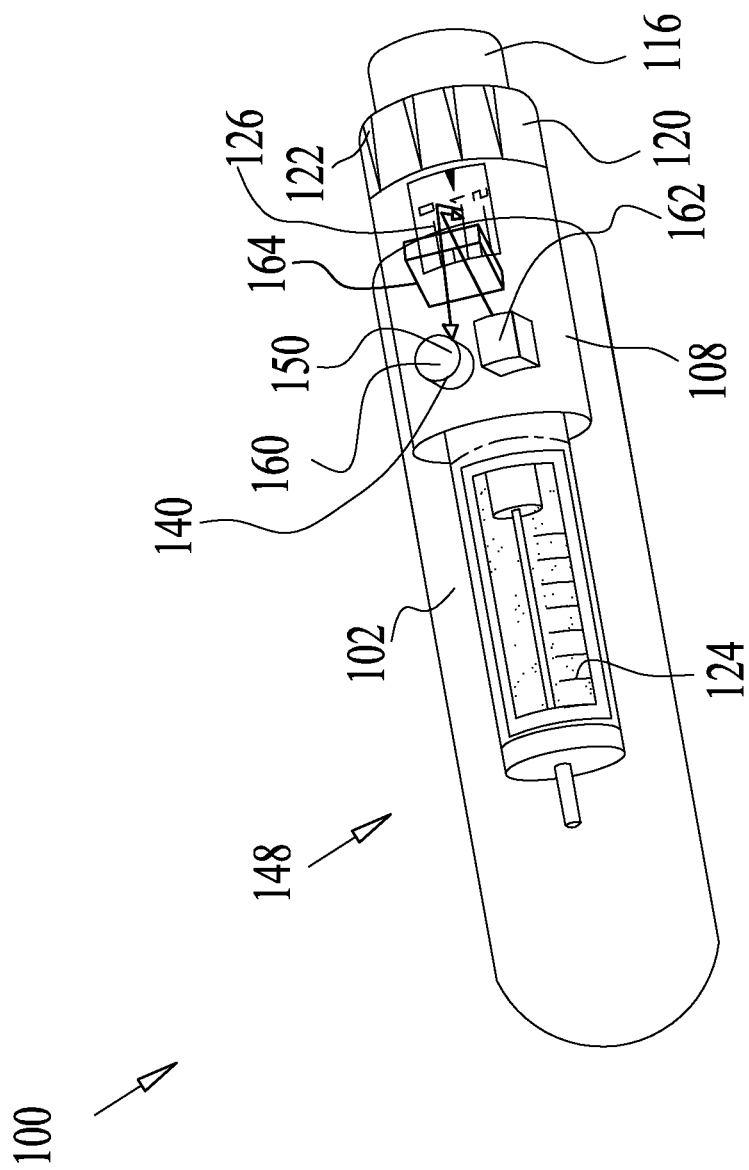
FIG. 11 is a schematic illustration of an exemplary drug dispensing-tracking system according to some embodiments of the present disclosure.
Figure 12:
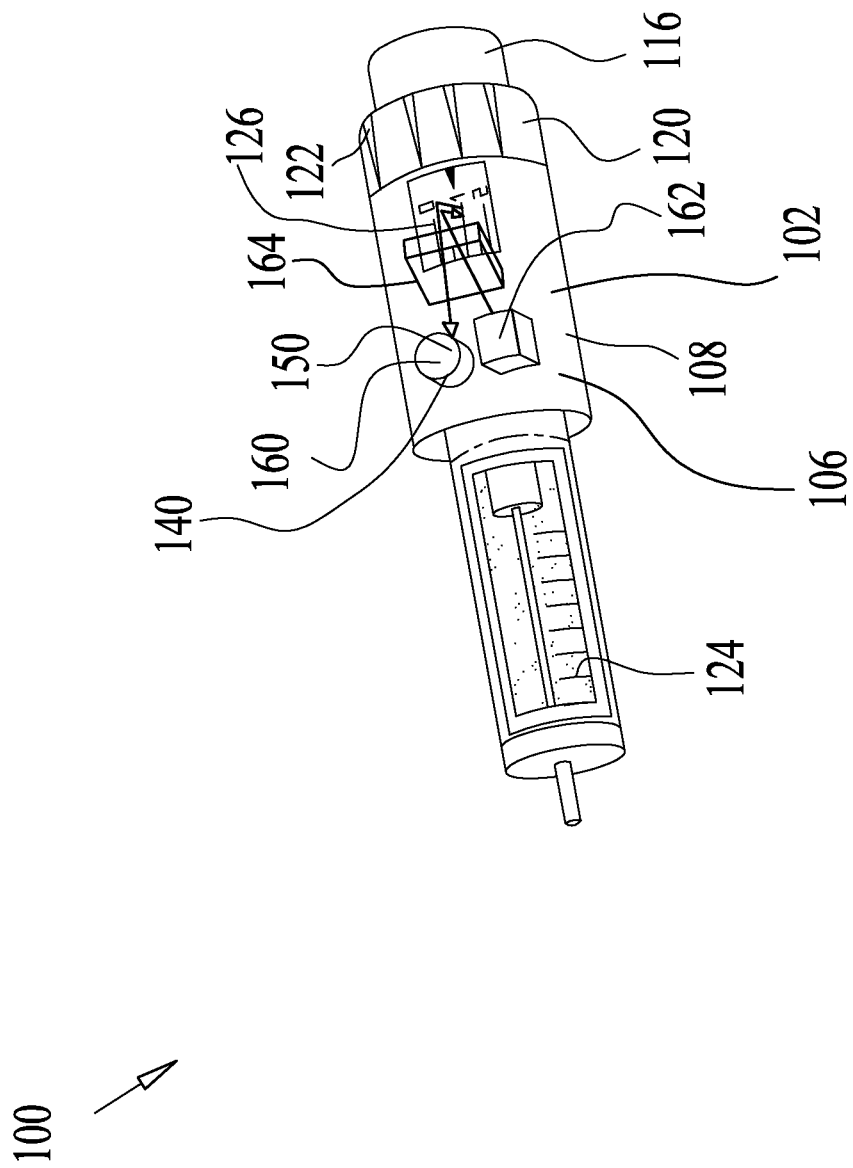
FIG. 12 is a schematic illustration of an exemplary drug dispensing-tracking system according to some embodiments of the present disclosure.

Turning to FIGS. 10-12, the optical sensor 150 may comprise an optical navigation-type sensor 160 (which may be referred to as an "optical navigation sensor"), such as used in a computer optical mouse. The optical sensor 160 is configured to detect the direction and distance magnitude of movement of a surface. The movement of a surface is measured by optically acquiring sequential surface images, processing image data and mathematically determining the direction and magnitude of the movement.

An exemplary optical sensor 160 may be an Avago Technologies ADNS-2080 sensor or ADNS-5050 sensor.

The optical sensor 160 may be placed on the elongated cylinder of shaft 108, such as on the outer cylinder 132 (FIG. 8B) or any other suitable location. In some embodiments, the optical sensor 160 may measure the direction and distance magnitude of rotation of the inner cylinder 129 (FIG. 8B) along rotation axis 138. Therefore measuring the magnitude of rotation may be indicative of the selected drug dose. As described, measuring the rotation direction to the first direction (e.g. clockwise) can indicate setting the drug dose to be dispensed from the drug reservoir 110 before the drug is injected. Measuring the rotation direction of the knob 120 to the second, opposite direction (e.g. counterclockwise) indicates correcting the dose by withdrawing the dispensed drug back to the drug reservoir 110.

A light source 162, such as an LED, illuminates a predetermined location on the inner cylinder 129, such as the scale markings 126 on the display window 130 or any other location. An optical device 164 may direct the light (shown by arrow 166 in the insert in FIG. 10) from the predetermined location to the optical sensor 160, for measuring the direction and magnitude of the rotation of the predetermined location. Optical device 164 may comprise a beam splitter or an optical lens or any other suitable optical device configured for directing light.

In some embodiments, the optical sensor 160 may measure movement along the longitudinal axis 139, thereby measuring the screw-like movement during rotation of the knob 120 and detecting the pressing of button 116 for injecting the drug.

Thus optical sensor 160 enables high precision detection of the selected dose and/or of an injection event.

The injection of the drug and the dose selection may be recorded, as will be further described, and may be used to notify the user of the time the drug was injected and/or the time duration since the last injection, as well as the dose.

In some embodiments, the optical navigation-type sensor 160 may be configured to detect movement of other components of the injection device 106, such as the plunger 114, for example.

The optical sensor 160, light source 162 and optical device 164 of the tracking device 102 may be formed within sleeve 134, as seen in FIG. 10. In some embodiments, the tracking device 102 may be formed in cap 148, as shown in FIG. 11. In some embodiments, the tracking device 102 may be formed as part of the injection device 106, as seen in FIG. 12.

Figure 13:
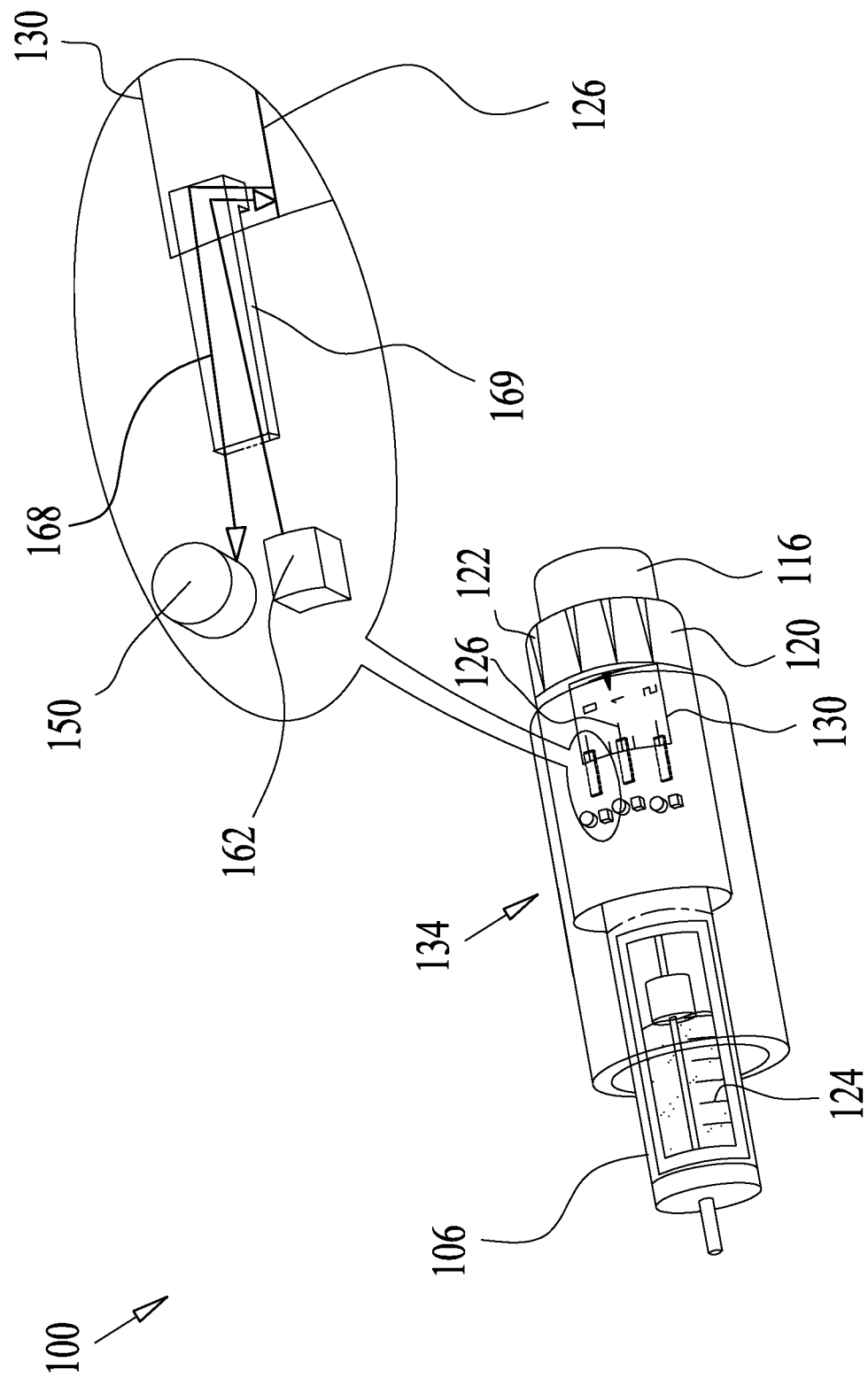
FIG. 13 is a schematic illustration of an exemplary drug dispensing-tracking system according to some embodiments of the present disclosure.
Figure 14:
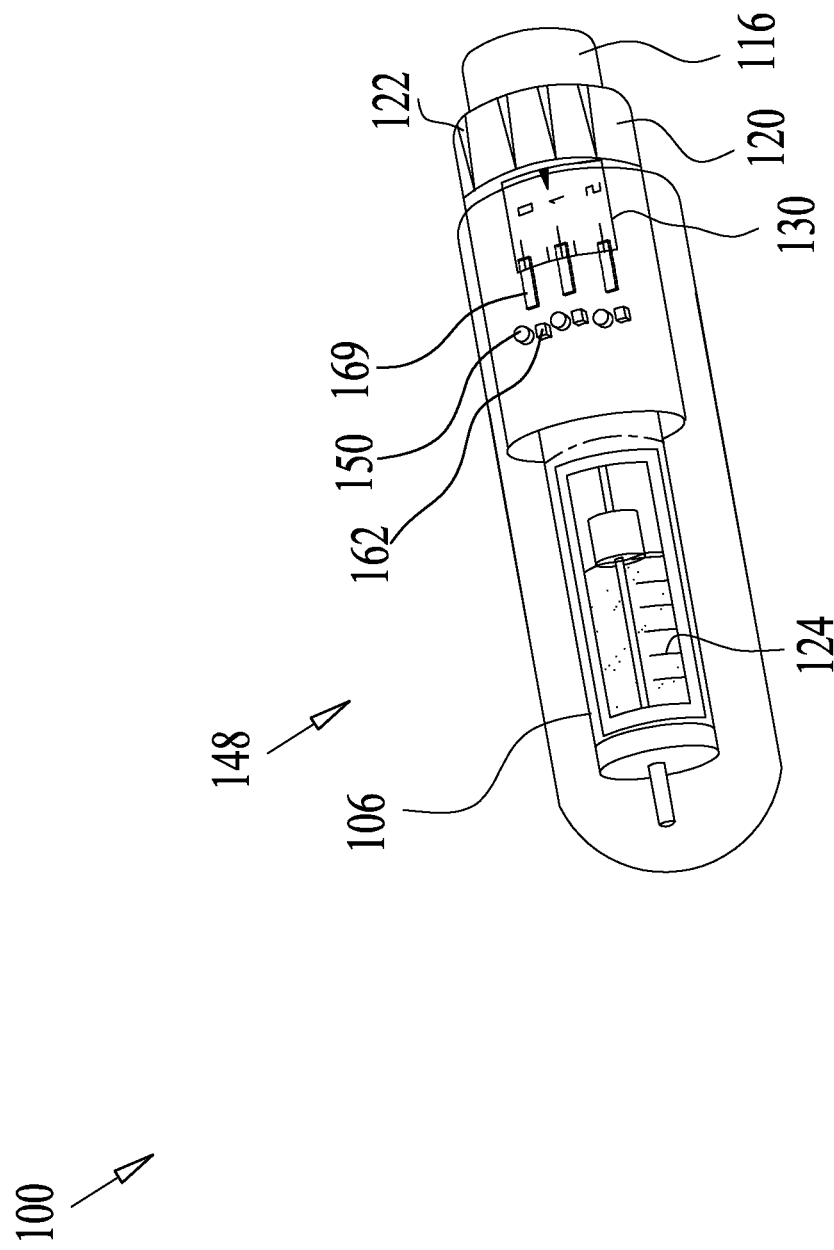
FIG. 14 is a schematic illustration of an exemplary drug dispensing-tracking system according to some embodiments of the present disclosure.
Figure 15:
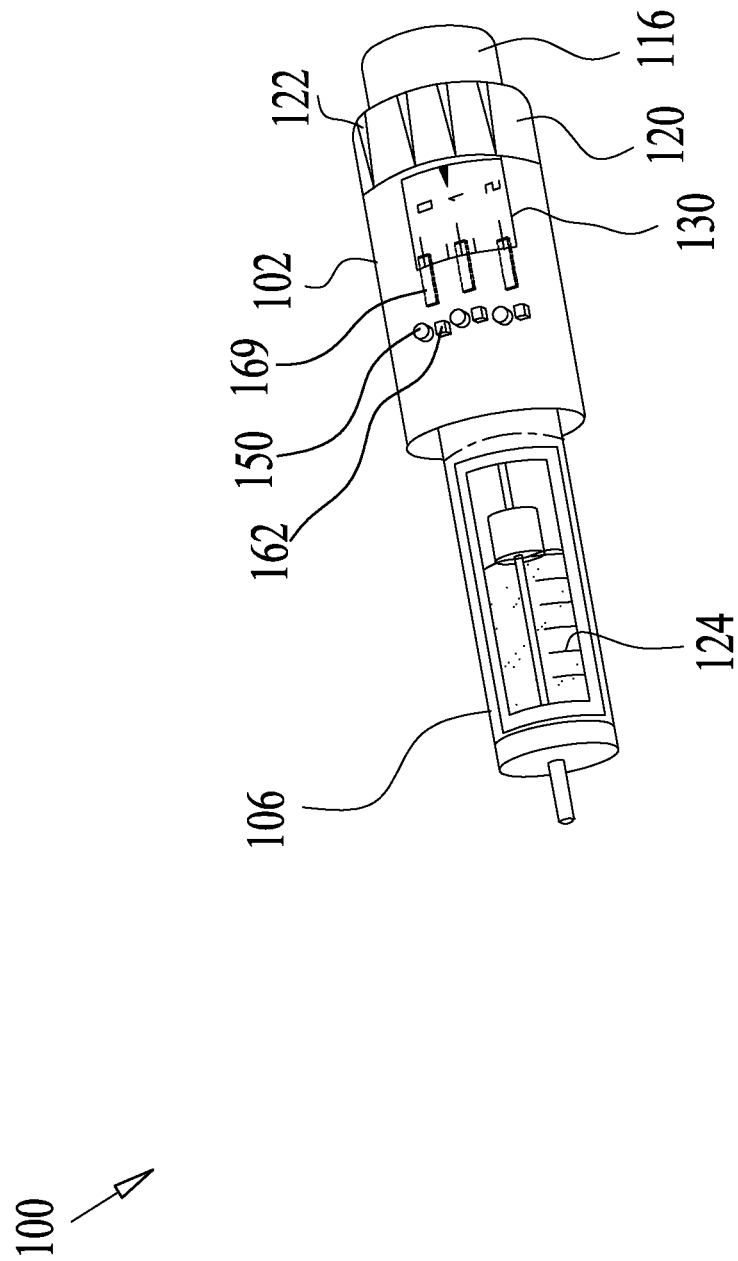
FIG. 15 is a schematic illustration of an exemplary drug dispensing-tracking system according to some embodiments of the present disclosure.

In FIGS. 13-15, the optical sensor 150 may be configured to detect changes in surface colors of the injection device 106, which are indicative of the selected drug dose and/or and injection event. In some embodiments, a light source 162, such as an LED, illuminates a predetermined location on the injection device 106, such as the scale markings 126 on the display window 130, as seen in the insert of FIG. 13. A light guide 169 or any light transmitting device, may transmit light (shown by arrow 168) from the predetermined location to an optical sensor 150. Rotation of the knob 120 concurrently moves the scale markings 126. The amount of light reflected from the surface of the scale marking 126, or of any other marking on the injection device 106, depends on the surface color. Namely, the scale markings may comprise color codes, such as the black color of the scale marking 126 and the white (or surface) color of the space between the scaling marking 126. Accordingly, when the scale marking 126 is positioned at the predetermined location, the surface color comprises black or a dark color of the scale marking 126. Light reflected by the light guide 169, when the scale marking 126 is positioned at the predetermined location (i.e. under the light guide 169), is less than the light reflected from a lighter surface, following rotation of the scale marking 126 away from the predetermined location.

The reflected light is detected by an optical sensor 150. The optical sensor 150 may comprise a photodetector, a CCD array 152 (FIGS. 6-9), an optical navigation-type sensor 160 (FIGS. 10-12) or any other light detecting configuration.

Positioning a plurality of light guides 169 over a plurality of predetermined locations on the cylinder enables detecting the number of scale markings 126 passing under the light guides 169, as well as detecting the rotation direction. As described herein, measuring the rotation direction to the first direction (e.g. clockwise) can indicate the setting of the drug dose to be dispensed from the drug reservoir 110, before the drug is injected. The rotation of the knob 120 to the second, opposite direction (e.g. counterclockwise) indicates correcting the dose by withdrawing the dispensed drug back to the drug reservoir 110.

In some embodiments, the optical sensor 150 receiving light from the light guides 169 may be configured to detect movement of other components of the injection device 106, such as the plunger 114, for example.

The optical sensor 150, light source 162 and light guides 169 of the tracking device 102 may be formed within sleeve 134, as seen in FIG. 13. In some embodiments, the tracking device 102 may be formed on cap 148, as seen in FIG. 14. In some embodiments, the tracking device 102 may be formed as part of the injection device 106, as seen in FIG. 15.

In some embodiments, the optical sensor 150 of any of FIGS. 6-15 may be configured to detect an optical signal including light of an invisible wavelength, to avoid detection of light from the ambient environment external to the injection device 106. In some embodiments, the optical signal may include light of a visible wavelength to aid a visually impaired patient or to allow a user to inject in a dark environment.

In some embodiments, to avoid detection of light from the ambient environment, the optical sensor 150 may be modulated to receive a modulated optical signal. In some embodiments, the tracking device 102 may comprise an optical modulator.

In some of the embodiments of FIGS. 6-15, the optical sensor 150 may detect drug related activities, such as by imaging visible indications on the injection device 106, such as capturing (e.g. by photographing) the scale markings 124, scale markings 126, or numerals 128. Further visible indications imaged by the optical sensor 150 may include the shaft transparent portion 112 filled with the drug or the shaft transparent portion 112 emptied of the drug. In some embodiments, for imaging the visible indications it may be sufficient to capture a single image (e.g. scale markings 126) without having to compare one image to a previous image.

In some embodiments, the optical sensor 150 may detect drug related activities, such as by imaging movement of the injection device 106 caused by selecting the drug dose (e.g. by turning the knob 120). The movement may include the movement of the plunger 114, the rotation of the knob 120, the movement of the inner cylinder 129 (e.g. by navigation-type optical sensor 160), and/or the movement of the scale markings 126 (e.g. by the light guide 169). In some embodiments, imaging the movement may include comparing one image to a previous image.

Figure 16:
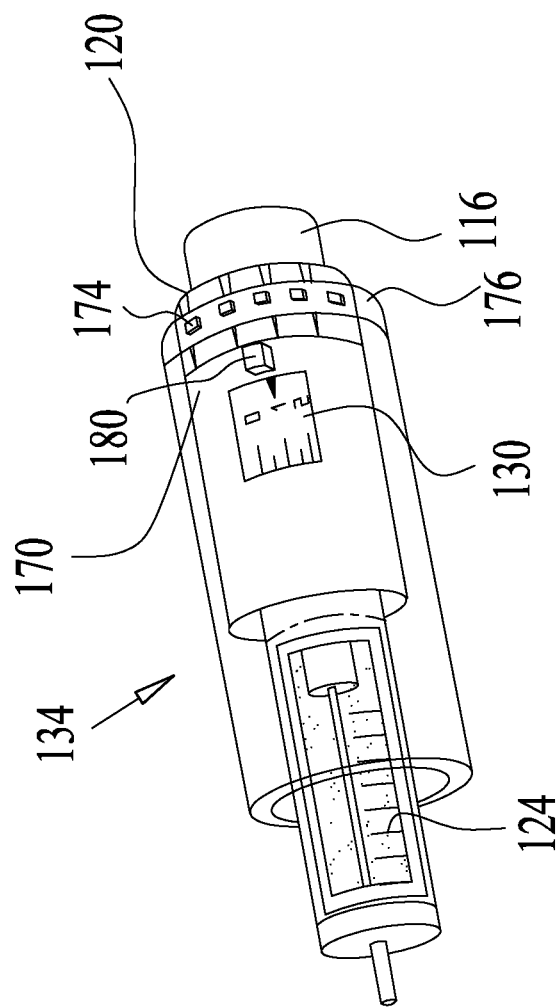
FIG. 16 is a schematic illustration of an exemplary drug dispensing-tracking system according to some embodiments of the present disclosure.
Figure 17:
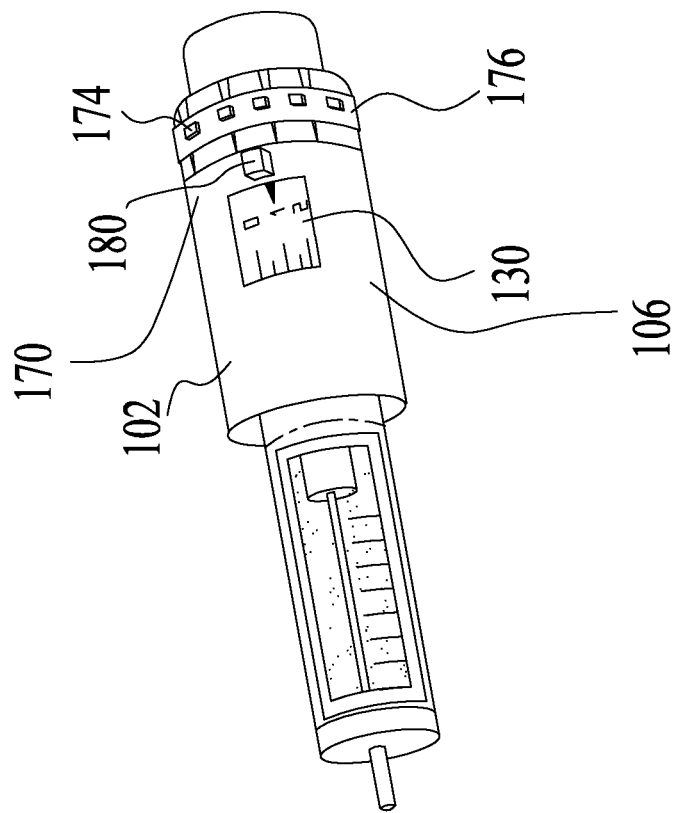
FIG. 17 is a schematic illustration of an exemplary drug dispensing-tracking system according to some embodiments of the present disclosure.

FIGS. 16 and 17 are schematic illustrations of an exemplary drug dispensing-tracking system according to some embodiments of the present disclosure.

In some embodiments, the signal may be a magnetic signal generated by an activity performed by the injection device 106. The magnetic signal may be indicative of the selected drug dose. As seen in FIGS. 16 and 17, the sensor 140 may comprise a magnetic sensor assembly 170 including at least one or more magnets 174 placed at any suitable location, such as on a ring 176 inserted on the knob 120.

In some embodiments, the magnets 174 may comprise permanent magnets configured to generate a magnetic field without required wiring or any power supply, as seen in FIGS. 16 and 17. In some embodiments, the magnetic field may be generated by coils, upon driving a current through the coils by a power supplier via electric wires.

A magnetic field sensor 180, formed in any suitable manner, may be placed at any suitable location, such as along shaft 108. The sensor 180 may comprise a sensing coil configured to detect changes in the magnetic field (or changes in the relative strength of the magnetic field) induced by angular displacement during rotation of the knob 120, thereby indicating the selected drug dose. Additionally, the sensor 180 may detect the direction of the rotation of the knob 120, which as described, may correspond to addition or removal of the drug for injection thereof. The magnetic sensor assembly 170 may comprise an electromagnetic encoder.

In some embodiments, the magnetic sensor assembly 170 may be configured to detect movement of other components of the injection device 106, such as the plunger 114, for example.

The magnetic sensor assembly 170 may be formed within sleeve 134, as shown in FIG. 16. In some embodiments, the magnetic sensor assembly 170 may be formed on cap 148. In some embodiments, the magnetic sensor assembly 170 may be formed as part of the injection device 106, as seen in FIG. 17.

In some embodiments, the placement of the notches 122 of the knob 120 may be imaged or detected in any suitable manner. The degree of placement of the notches 122 may correspond to a dose of drug units injected and thus may be indicative of the dose of the injected drug.

In some embodiments, the signal may be a movement signal generated by an activity performed by the injection device 106. The sensor 140 may comprise a movement sensor for detecting the displacement caused by the activity of the injection device 106, such as the rotation of the knob 120 and/or the pressing of the button 116. In some embodiments, the number of clicks detected by the displacement sensor may indicate the dose of drug injected by the user. Additionally, the displacement sensor may detect the direction of the rotation of the knob 120, which as described, may correspond to addition or removal of the drug for injection thereof.

In some embodiments, the movement sensor may comprise an electromechanical sensor, an optical sensor, an optical navigation sensor, a microphone, a vibration sensor, an accelerometer, a rotational sensor, an angular rotation sensor, a combination thereof or any other suitable sensor for detecting movement of the injection device 106 or any other activity related thereto. For example, a laser diode and an optical detector may be used for detecting movement.

FIGS. 18-20 are schematic illustrations of an exemplary drug dispensing-tracking system according to some embodiments of the present disclosure.

In some embodiments, the tracking device 102 may comprise a combination of types of sensors for detecting different types of signals. In a non-limiting example, as seen in FIG. 18, the tracking device 102 comprises the acoustic sensor 144 (FIG. 3) or the vibration sensor 146 (FIG. 4) as well as the optical sensor 150 (FIGS. 6-15). A plurality of acoustic/vibration sensors 144 or 146 and a plurality of optical sensors 150 may be arranged to capture more than one signal indicative of the injection activity, such as the drug dose. For example, the different sensors may be positioned on the tracking device 102 asymmetrically along the rotation axis 138 and/or the longitudinal axis 139 (FIG. 10) so as to capture the signals from a plurality of different locations to achieve higher accuracy.

In some embodiments, the plurality of sensors 140 are arranged in an array. In some embodiments, the plurality of sensors 140 are spaced apart along and/or around the tracking device 102.

The acoustic sensor 144 or the vibration sensor 146 as well as the optical sensor 150 or any combination of sensors 140 may be formed within sleeve 134, as shown in FIG. 18. In some embodiments, the combination of sensors 140 may be formed on cap 148, as shown in FIG. 19. In some embodiments, the combination of sensors 140 may be formed as part of the injection device 106, as shown in FIG. 20.

Using a combination of sensor types or using more than a single sensor 140, even of the same type, enhances the dose detection accuracy (or any other drug related activity) and minimizes detection of false signals. For example, auditory signals may be falsely detected by the acoustic sensor 144. These false signals may be filtered by an accompanying optical sensor 150.

In some embodiments, the tracking device 102 may comprise a combination of types of sensors or even the same type sensor configured for detecting different types of signals from the same or different components of the tracking device 102. For example, the CCD array 152 may be configured to image the scale marking 126 as well and the drug filling the transparent portion 112. The different received signals may be juxtaposed, thereby enhancing the dose detection accuracy (or any other drug related activity) and minimizing detection of false signals.

Achieving accurate drug dose detection is of paramount importance in disease treatment management. The accuracy level of detecting the drug dose by using any one of the tracking devices 102 of FIGS. 1-20 is relatively high. For example, the accuracy level may be of a few drug units, a single drug unit or a half of a drug unit. In a non-limiting example, wherein the drug is insulin, a drug volume of 1 unit (IU) of insulin, is 0.01 milliliters. An injection pen, a cartridge or a syringe may hold 150 or 300 units of insulin. Thus, the accuracy level using insulin can be a few IUs, a single drug unit (1 IU, 0.01 millileters), or half of a drug unit (0.5 IU, 0.005 millileters).

In some embodiments, a first type of sensor 140 may prompt the activation of a second type of sensor 140. For example, upon detecting the selection of the dose or any other injection related activity, by a relatively cheap sensor, a dormant, relatively expensive sensor may be prompted to commence its operation. In a non-limiting example, the light source 154 and the CCD array 152 in FIGS. 18-20 may be configured to be inactive while injection activity remains undetected. Upon detection of rotation of the knob 120 by the microphone 144, the light source 152 illuminates and the CCD 150 is activated.

The detection of the drug dose or any other drug related activity may be performed by many methods described herein, such as in reference to FIGS. 1-20. In some embodiments the scale marks 124 or 126 appearing on a standard injection device 106 may be detected and are indicative of the drug dose or any other drug related activity. For example, the CCD array 152 may image the scale marks 124 or the scale marks 126. In some embodiments, the movement of the scale marks 126 on the inner cylinder 129 may be detected, such as by the navigation-type optical sensor 160 of FIGS. 10-12 or by any other type of optical sensor, such as a CCD array 152. In some embodiments, movement of the scale markings 126 may be measured by detecting surface color changes using the light guide 169 and optical sensor 150 in FIGS. 13-15 or by any other suitable means, such as by the CCD array 152.

In some embodiments, turning of the knob 120 or movement of the injection device 106 caused by turning the knob 120 may be detected and is indicative of the drug dose or any other drug related activity. This may include, for example, measuring the movement of the plunger 114, such as by a CCD array 152. In some embodiments the rotation of the knob 120 may be measured by imaging the knob 120 using a CCD array 152, by using a magnetic sensor assembly 170 (FIGS. 16-17) or by an acoustic sensor 144 (FIGS. 2-3) or vibration sensor 146 (FIG. 4). The movement of the inner cylinder 129 may be measured, such as by navigation-type optical sensor 160 of FIGS. 10-12 or by any other suitable means, such as by imaging the inner cylinder 129 with a CCD array 152. In some embodiments, the movement of the scale markings 126 may be detected, such as by detecting surface color changes using the light guide 169 and optical sensor 150 in FIGS. 13-15, or by any other suitable means.

The tracking device 102 of FIGS. 1-25 may comprise additional features for transferring data indicative of the detected signals. Some of these features are shown in FIGS. 2 and 3 it being appreciated that the tracking device 102 of any of FIGS. 1-25 may comprise these features. In some embodiments, the sensor 140, upon detecting the selected dose of drug or any other injection activity, may inform the user, via a speaker 190 (FIG. 2) or by any other announcement means (such as, for example, text or audio from external unit 204 (FIG. 3)). This enables visually impaired insulin dependent diabetics to correctly set the injection device 106 to the correct dose.

In some embodiments, the tracking device 102 may comprise an identifier 192 comprising any suitable component for identifying the tracking device 102 and/or the injection device 106. In a non-limiting example, the identifier may comprise an RFID sticker and/or a Subscriber Identification Module (SIM) card.

In some embodiments, the tracking device 102 may comprise a display window 194. The detected information, such as the selected drug dose, or any other information, may be displayed on the tracking device display window 194.

The tracking device 102 may comprise controllers and electronics, such as a thermistor, a transistor, boards, wires or circuitry.

In some embodiments, the tracking device 102 may comprise electrical components and a transmission element 200 (FIG. 2) for transmitting the detected signal or data related thereto to an external unit 204 (FIG. 3). The transmission element 200 may comprise any element configured to pass the signal from the tracking device 102 thereon. The transmission element 200 may comprise for example, a transmitter, a transceiver, a transponder, an antenna, a transducer, and/or an RLC circuit. The electrical components may comprise any suitable components for detecting, processing, storing and/or transmitting a signal, such as electrical circuitry, an analog-to-digital (A/D) converter, and an electrical circuit for analog or digital short range communication, for example.

The transceiver may be configured for at least one of transmitting and receiving information to/from a wireless device. The computer instructions may be additionally configured to cause the processor to transmit the information via the transceiver to a wireless device. The computer instructions may be additionally configured to cause the processor to transmit the information via a transceiver or wireline connection to a second device, such as the external unit 204 or central database 208. The second device may be configured to alert a user of the information.

The second device may be configured to be displayed via at least one of the second device and a third device. The third device may comprise the external unit 204 or central database 208 or any other device.

The external unit 204 may be any apparatus configured to receive the detected signal or data related thereto for processing thereof. The external unit 204, in some embodiments, may be configured for further transmitting the detected signal or data related thereto to a central database 208. In some embodiments, the external unit 204 may comprise any of a computer, PC, laptop, tablet, a cellular phone, a smartphone, media player, personal data assistant ("PDA"), and/or the like. In some embodiments, the external unit 204 may comprise a glucose meter.

In some embodiments, the external unit 204 may comprise a treatment device 210 (FIG. 25) worn on the skin of a user to treat an injection site to improve the pharmacodynamics or pharmacokinetics of the drug. The injection site may be an intradermal layer. The treatment device 210 may comprise a treatment device, such as INSUPAD®, disclosed in Applicant's PCT patent applications PCT/IB2008/051044, PCT/IB2009/007600, and/or PCT/IB2012/052335, each of which is incorporated herein by reference in their entireties. The tracking device may comprise a tracking device disclosed in Applicant's PCT patent application PCT/IL2013/050857 incorporated herein by reference in its entirety.

The central database 208 may comprise any suitable device or function for storage of the data and/or analysis thereof. The central database 208 may comprise a processor and/or memory. In a non-limiting example the central database 208 may comprise a computer, PC, laptop, tablet, smartphone, media player or personal data assistant ("PDA"). The drug dispensing-tracking system 100 may comprise a processor for processing the detected signal and/or data received from the tracking device 102. The processor may have operating thereon computer instructions for causing the processor to perform at least one of: receive, transmit, analyze and/or store information, at least a portion of the information comprising at least one of: the at least one respective signal, a time corresponding to the at least one respective signal, an amount of drug injected by the drug-injection device, an amount of drug remaining in a reservoir associated with the drug-injection device following one or more drug injections, a duration since a previous injection; an age and/or expiration of the drug; a period of time since the manufacture of the drug; a bio-potency/availability of the drug; a quality of the drug; a degree of cloudiness of the drug; a temperature of drug; identification of the injection device; and/or identification of the tracking device.

A memory may also be provided for storing the detected signal and/or data.

In some embodiments, the external unit 204 may comprise a processor 212. The sensor 140 may generate a second signal in response to the detected signal. The second signal may be transmitted via transmission element 200 to the external unit 204. The external unit processor 212 may process and analyze the second signal and convert it to data. The data may be transmitted to the central database 208. In such embodiments, the data may be transmitted to the central database 208 at the time the detected signal is generated, namely, transmission in real-time.

In some embodiments, the data may be relayed via wireless or wired connection by the external unit 204 to the central database 208.

In some embodiments, the external unit 204 may comprise a memory 214. The data may be stored in the memory 214 and may be transmitted thereafter to the central database 208.

In some embodiments, the tracking device may comprise a processor 220. The detected signal and/or the second signal may be processed and analyzed and converted to data by the processor 220. The data may be transmitted to the external unit 204 or may be first stored in a memory 222 of the tracking device 102 and thereafter may be transmitted from the tracking device memory 222 the external unit 204. In one embodiment, the external unit 204 may transmit the data to the central database 208. In another embodiment, the data may be further processed by the injection device processor 220 and thereafter may be transmitted to the central database 208. In another embodiment, the data may be further processed by the external unit processor 212, stored in the external unit memory 214 and thereafter may be transmitted to the central database 208. In another embodiment, the data may be transmitted from the tracking device processor 220 or the tracking device memory 222 directly to the central database 208 or concurrently with transmission to the external unit 204.

In accordance with the system and method of the disclosure, the sensor 140 may be configured to detect signals in any suitable detection pattern determining the detection duration and frequency of detection in the duration. Some exemplary detection patterns may be selected as follows:

In some embodiments, the sensor 140 may be frequently or periodically sampled by the tracking device processor 220 and/or external unit processor 212.

In some embodiments, the sensor 140 may be configured to detect a signal automatically, such as upon an injection event or activity and/or at predetermined time periods. The injection event may include the injection of the drug. An example of a tracking device 102 detecting a signal upon use of the injection device 106 is described in reference to FIGS. 22A-23. Another example includes detecting the rotation of the knob 120 or pressing the button 116.

In some embodiments, the sensor 140 may be configured to detect a signal automatically, such as upon a pre-injection event proceeding or anticipating the injection event. For example, the tracking device 102 may comprise an element (e.g., a sensor 140) configured for the automatic detection of an injection event (e.g., by an injection event sensor). This element may be monitored by processor 220 via software associated therewith to sense when an injection activity is performed. The injection event sensor may be prompted by communication between the electrical components of the tracking device 102 and electrical components of the external unit 204. For example, when the external unit 204 comprises a blood glucose meter, the injection event sensor may detect a blood glucose measurement. When the external unit comprises a treatment device 210 (FIG. 25), the injection event sensor may detect activation of the treatment device 210. Since the activity of the external unit 204 (e.g.

a blood glucose measurement or activation of the treatment device 210) occurs prior to the injection activity, in some embodiments, this activity may be used to signal that an injection is expected to be performed, thereby activating sensor 140. According to this embodiment, the detection occurs around the injection event, thus reducing unnecessary detection, and hence preserving the operation power of the tracking device 102.

In some embodiments, the sensor 140 may be frequently or periodically sampled by the tracking device processor 220 and/or external unit processor 212.

In some embodiments, the tracking device 102 may be preset to detect at predetermined time intervals. For example, when tracking insulin, the tracking device 102 may have predetermined time intervals scheduled generally at time intervals when basal drug doses are injected, such as, for example, in the morning and/or at night.

In some embodiments, the tracking device 102 may comprise a switch 228 (FIG. 2) or a component configured to prompt the sensor 140 to detect a signal. The switch 228 may be switched on by a user or in response to any other event, such as by a signal provided by the external unit 204. For example, when the external unit 204 comprises a treatment device 210 (FIG. 25), the operation of the treatment device 210 may be used to switch on the switch 228.

In some embodiments, the switch 228 may be toggled between two or more states by the user, including, for example, a state for switching on the tracking device 102 and turning off the tracking device 102. The switch 228 may be toggled between an "off" state and an "on" state in response to any suitable trigger, such as the operation of the injection device 106 or the rotation direction of the rotation knob 120. In some embodiments, the states may comprise at least one of: a state for turning on the tracking device 102, a state indicating the direction of the injection device movement as it is set by the user to the dose of the injected drug, a state indicating re-adjustment of a dose of drug before injection, and a state indicating the drug is to be injected.

In some embodiments, the external unit 204 may comprise a switch or a component configured to detect the second signal transmitted from the tracking device 102.

In some embodiments, the external unit 204 may include a proximity detector for detecting the presence of the tracking device 102 when in proximity thereto, thereby triggering the external unit 204 to detect the second signal transmitted from the tracking device 102.

In accordance with an embodiment, when the injection is performed, the electronics of the tracking device 102 may wirelessly transmit by transmission methods, the signal created (e.g. auditory, vibration, optical, magnetic) to the external unit 204. The processor 212 of the external unit 204 may analyze the information to determine the dose of drug injected and either store the information in an external unit memory 214 for later download, or transmit the information in real-time to the central database 208.

In accordance with some embodiments, the sensor 140, such as microphones 144, may be frequently sampled by the processor 220 (FIG. 2) of the tracking device 102 to analyze the signal created when the rotation knob 120 of the injection device 106 is turned in order to detect an injection event. When the user "sets" the injection device 106, the sensor 140 may pick up the signal created during the setting event. When the processor 220 analyzes that the setting event is completed, it may be configured to activate the transmission element 200. The signal created (or corresponding data associated therewith) when the drug is injected, may then be transmitted wirelessly (e.g., via WiFi, Bluetooth, and/or the like) to the external unit 204. The processor 212 of the external unit 204 may analyze the received signal/data to determine the dose of drug that was just injected.

In some embodiments, in order to preserve battery power the transmission element 200 may be turned on following detection of an injection event or detecting readying the injection device 106 for an injection. The detection of the injection event may be performed by detecting the pressing of the button 116, as described herein. Detecting readying the injection device 106 for an injection may be performed by detecting the selection of the dose, such as by detecting the rotation of the knob 120, as described herein.

In some embodiments, injection devices 106 may include the protective cap 136 that is removed before injection is made. Therefore, in accordance with some embodiments of the present disclosure, the tracking device components, such as electronics, may be turned "on" upon removal of the cap 136. The signal/data may be then transmitted wirelessly to the external unit 204 to be analyzed in order to determine the dose of drug that was just injected.

In accordance with an embodiment of the present disclosure, the tracking device 102 may be formed with a mechanical attachment to the injection device 106. The mechanical attachment can be separated to a part which fits the cap 136 (shown in FIG. 22B as second section 258) and a part (shown as first section 254) that fits the injection device body (e.g. the shaft 108). The part which fits the cap 136 may have at least one activation pin 262 extending out therefrom. These one or more activation pins 262 may contact the switch 228 (FIG. 2) inside the part of the tracking device 102 that mechanically fits the injection device body (e.g. the shaft 108). When a user removes the cap 136 to inject the drug, the activation pin 262 disconnects from the switch 228 and this may turn on the electrical components of the circuit on the tracking device part 254 which fits the injection device body. This may be configured to thereby activate the sensor 140, the transmitter and/or transponder, and in some embodiments, the processor 212 or processor 220, to measure the dose of drug that was injected and transmits the data to the external unit 204.

In some embodiments, the injection device 106 may be provided with wireless cellular capabilities. In such injection devices 106, with each injection, the injection information may be wirelessly transmitted and logged in the central database 208 or external unit 204 for real-time analysis and feedback to the user.

In some embodiments, the transmission of data or signal from the injection device electronics to the external unit 204 may be performed using any of Bluetooth short range digital communication modes or an analog communication mode.

In some embodiments, external unit 204 may be set to detect a signal coming from the injection device 106 at predetermined times or following certain activity of the external unit 204. Such activity of the external unit 204 can be, for example in the case of an INSUPAD, activation of the INSUPAD just before injection, which in a certain configuration of the INSUPAD is performed by opening the INSUPAD to reveal an injection window. In case the external unit 204 comprises a blood glucose meter, the activity can include performing a blood glucose measurement, which is usually performed before injection. In the case of predetermined time intervals, they can be preset to be in the morning or night, and will be used to detect basal injections which are usually given during these time periods.

In some embodiments, the external unit 204 may comprise a button which is pressed by the user to move the unit to a mode where it is ready to detect the signal coming from the tracking device 102.

In some embodiments, the external unit 204 may comprise a proximity detector which may detect the presence of the tracking device 102 in proximity thereto and trigger a receiver of the external unit 204 to detect the signals coming from the tracking device 102.

In some embodiments, any combination of the preceding methods can be used in order to move the external unit 204 to a mode where it is ready to detect the signals coming from the tracking device 102 and determine the dose of drug that was injected or determine any other injection related activity.

In some embodiments, the processor that analyzes the signal to determine the dose of insulin injected may use an algorithm that detects the different impulses present in the signal that are associated with the different insulin units that were injected. Those signal impulses can be detected during the initial settings of the dose when rotating the knob 120 to its initial pre-injection stage. Those signal impulses can be detected during the injection step when the knob 120 is pressed and the drug injected and a series of sound clicks is heard or any other signal is detected. Those sound impulses can be detected also from both the sound clicks during initial dose setting and during the injection event.

In some embodiments, the processor which analyzes the signal to determine the dose of injected drug, may use a simple comparison algorithm where a sequence of signal impulses is compared to a sequence of pre-recorded impulses to determine the dose of drug injected. The memory of the processor may contain multiple signal samples, such as sound samples for each dose which can be injected by the specific type of injection device 106.

The data may comprise any data related to the activity of the injection device 106 and/or the drug, which may comprise, inter alia, the injected dose of a drug; the amount of drug remaining in the injection device 106 following the drug injection; the amount of drug remaining in a reservoir associated with the injection device 106 following one or more drug injections; the time of injection; the time duration since the previous injection; the age or expiration of the drug, such as the time passed since the manufacturing of drug; a period of time since the manufacture of the drug; the bio-potency/availability of the drug; a quality of the drug; the optical quality of the drug; the degree of cloudiness of drug; the temperature of drug; setting the injection device 106 for dispensing the drug; the dispensing action of the injection device 106 or the flow of the drug into a user; identification of the injection device; identification of the tracking device 102 and/or the like.

The data may further comprise information related to the type of drug as well as identification of the injection device 106 and/or the tracking device 102. In the treatment course of a diabetic patient, different types and/or quantities if insulin are administrated, such as a basal insulin dose and a bolus insulin dose. The different doses may be injected by different injection devices 106. Therefore, data indicating the type of injected dose assists the user, caretaker or physician in monitoring the course of correct treatment.

In some embodiments, the data may comprise time information corresponding to the date and time of a respective injection.

In some embodiments, the tracking device 102 and or the external unit 204 may be programmed to anticipate injection of the drug at predetermined periods and with a predetermined dose. Accordingly, the data may also indicate omission of an anticipated injection or incorrect dosage.

In some embodiments, the data may be used to monitor the expiration of the drug. This may be determined by measuring the time discrepancy between the first use of the injection device 106 and a current time or by comparing the date of the drug injection with an expiration date provided by the drug manufacturer.

In some embodiments, the tracking device 102 may include a temperature sensor and the data may detect the temperature of the drug and/or the ambient environment. The temperature measurement may be used to indicate overheating and hence inefficacy of the drug (i.e., a drug that has been overheated may become less effective). In some embodiments, when the external unit comprises a treatment device 210 (FIG. 25) utilizing heat, the temperature sensor may detect the temperature of the treatment device 210, thereby ensuring the treatment device operates properly and/or possibly adjusts the treatment device 210 accordingly.

The detected signal, second signal and/or data may be transmitted from the tracking device 102 to the external unit 204, and to the central database 208; and/or from the tracking device 102 to the central database 208 in any suitable manner, such as wirelessly, via an analog short range communication mode, or a digital communication mode including WIFI or Bluetooth, or via a wired connection. Additional examples for transmission may be via a network. The network may comprise a local area network (LAN), a wide area network (WAN), or a global network, for example. The network may be part of, or comprise any suitable networking system, such as the Internet, for example, or an Intranet. Generally, the term "Internet" may refer to the worldwide collection of networks, gateways, routers, and computers that use Transmission Control Protocol/Internet Protocol ("TCP/IP") and other packet based protocols to communicate therebetween.

The data may be used by a physician, caretaker or the patient to track treatment goals. The data may be used with data provided by the glucose meter. Additionally, the data may be used to alert the patient upon passage of the drug expiration date. Moreover the data may be used to alert the patient upon reduction of the efficacy of the drug due to excess heat or any other relevant parameter.

In some embodiments, placement of the tracking device 102, such as sleeve 134 or cap 148 on an injection device 106 may trigger a process urging the user to indicate if the injection device 106 is new or was in use. The type of injection device 106 and drug (e.g. insulin) and the drug dose (or amount of drug present in the injection device 106) may be recorded upon this process by a dedicated application operating on the external unit 204, such as a smartphone, for example, or by any other suitable means.

In some embodiments, information is transmitted to an application operating on a mobile device. The application causes the mobile device to output information to inform a user or other person of at least one of: a time corresponding an injection, an amount of drug injected by the drug-injection device, an amount of drug remaining in a reservoir associated with the drug-injection device following one or more drug injections, a duration since a previous injection; an age and/or expiration of the drug, a period of time since the manufacture of the drug, a bio-potency/availability of the drug, a quality of the drug, a degree of cloudiness of drug, a temperature of the drug, identification of the injection device, identification of the tracking device.

In some embodiments, the removal and/or insertion of a drug vial may be detected in any suitable manner. For example, the CCD array 152 may be provided to optically capture (e.g. photoimage) the removal and/or insertion of a drug vial. In some embodiments, detection of the removal and/or insertion of a drug vial may comprise capturing the dose of drug in the vial or position of a vial piston 114 (FIGS. 6-9). The sensor 140 may comprise a pressure sensor, which may be used to detect the removal and/or insertion of a drug vial.

Insertion of a new drug vial may prompt recording information relating to the new drug vial. For example, the user may be prompted by the external unit 204 to enter the information in any suitable manner, by typing in the information and/or by vocal recording. The information may be entered into the external unit 204, the central database 208 or any suitable means. The drug vial information may include the expiry date, the batch lot, size, brand name, manufacturing date, and/or any other suitable information. In another example, the drug vial information may be recorded by photographing the drug vial or the drug vial box using the CCD array 152 or a camera on the external unit 204. The external unit 204, and/or the central database 208 may be configured to properly store the drug vial information in computer readable form. This can be performed without human intervention.

In some embodiments, the age of the drug can be determined by detecting the time of the injection event, as described herein, and calculating the time that has passed from the manufacturing of the drug to the detected injection.

In some embodiments, the drug vial information may include the dose of drug remaining following injection thereof. This allows the user to record the dose of drug that was injected by subtracting the dose of remaining drug from the original, full amount of drug in the vial. The original, full amount of drug in the vial may be recorded by the user or may be derived from the barcode or brand name of the vial or by any other suitable manner.

The CCD array 152 may comprise infrared imaging capabilities allowing imaging of the vial from the sleeve 134.

In some embodiments, the weight of the injection device 106 or a component thereof, such as the shaft 108, may be measured to calculate the dose of injected drug, by comparing the weight of the drug before and after injection. In some embodiments, weighing the injection device 106 may be performed in a load cell or by any other suitable device.

In some embodiments, the sensor 140 may comprise a temperature sensor formed in any suitable manner. In a non-limiting example, the temperature sensor may comprise a thermistor, or may be a passive sensor which is configured to change a physical property thereof (e.g. color) to indicate a change in temperature or going over a temperature threshold or being above a temperature threshold more than a predetermined time duration.

In some embodiments, the user may be alerted upon detection of changes in the temperature of the drug. The temperature of the drug may be provided to the user, in any suitable manner, such as on the display 130, the tracking device display 194, via the external unit 204 and/or via the central database 208. The bio-potency of the drug may be affected by changes in temperature. In some embodiments, the detected change in the drug temperature may prompt the user to be alerted and informed of the degree of the current bio-potency of the drug. For example, an alert may inform the user that the bio-potency of the drug has been reduced to 95%, or to 90%, or to 85%, and lower. In some embodiments upon reaching a predetermined bio-potency threshold the user may be alerted that the drug bio-potency has significantly diminished. The alert may be generated in any suitable form, such as a textual message shown in window display 130, tracking device display 194, and/or a textual or verbal message provided by the external unit 204. In calculating the remaining bio-potency, the system 100 may use the information of the temperature profile (such as the temperature degree and the duration of exposure) that the drug was exposed to by taking into account both the temperature and duration of exposure to the different temperatures.

Figure 21:
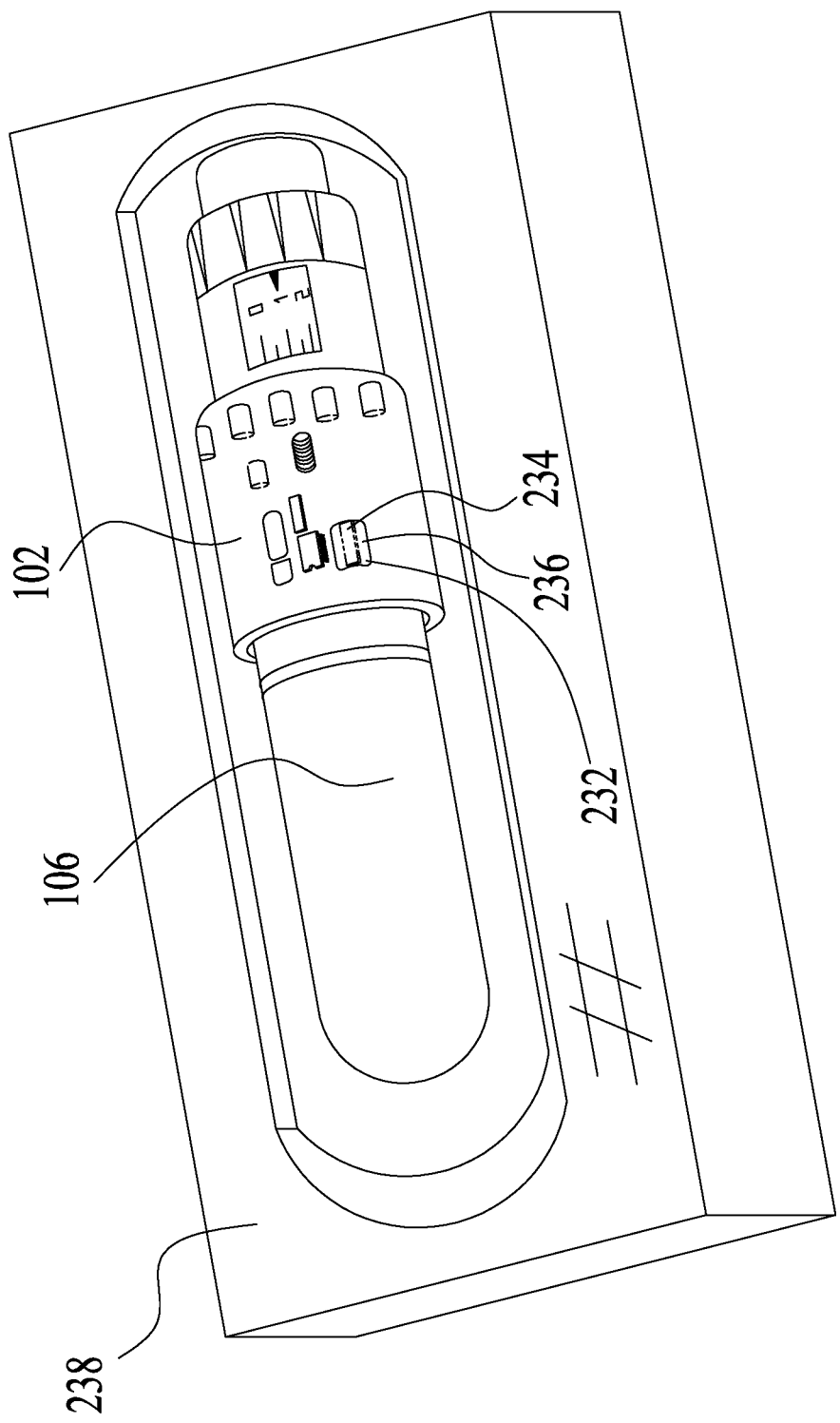
FIG. 21 is a schematic illustration of an exemplary drug dispensing-tracking system according to some embodiments of the present disclosure.

The tracking device 102 may operate using any suitable power source 232 (FIG. 2), such as a battery 234. In some embodiments the tracking device 102 may comprise a battery enclosure 236 for removing a discharged battery 234 and replacing it with a new battery. In some embodiments, the battery 234 may be recharged by inserting the tracking device 102 (and, in some embodiments, the injection device 106) on a recharging cradle 238, as shown in FIG. 21. In another embodiment, the tracking device 102 may be connected to a power source via a cable. In some embodiments, the battery 234 may be recharged by induction.

In some embodiments, the sleeve 134 and/or the cap 148 may be configured to connect with a mechanical feature of the injection device 106, removably or non-removably (i.e., permanently). In some embodiments, the tracking device may comprise a housing with one or more clamps (or clamp-like elements), for affixing (either permanently or non-permanently) to an injection device.

In some embodiments the sleeve 134 and/or the cap 148 may be configured for removable or permanent connection with a mechanical feature or shape of the injection device 106, such that the shaft movement during an injection is not affected, and ease of use and accuracy of the injection device 106 may be maintained.

Figure 22A:
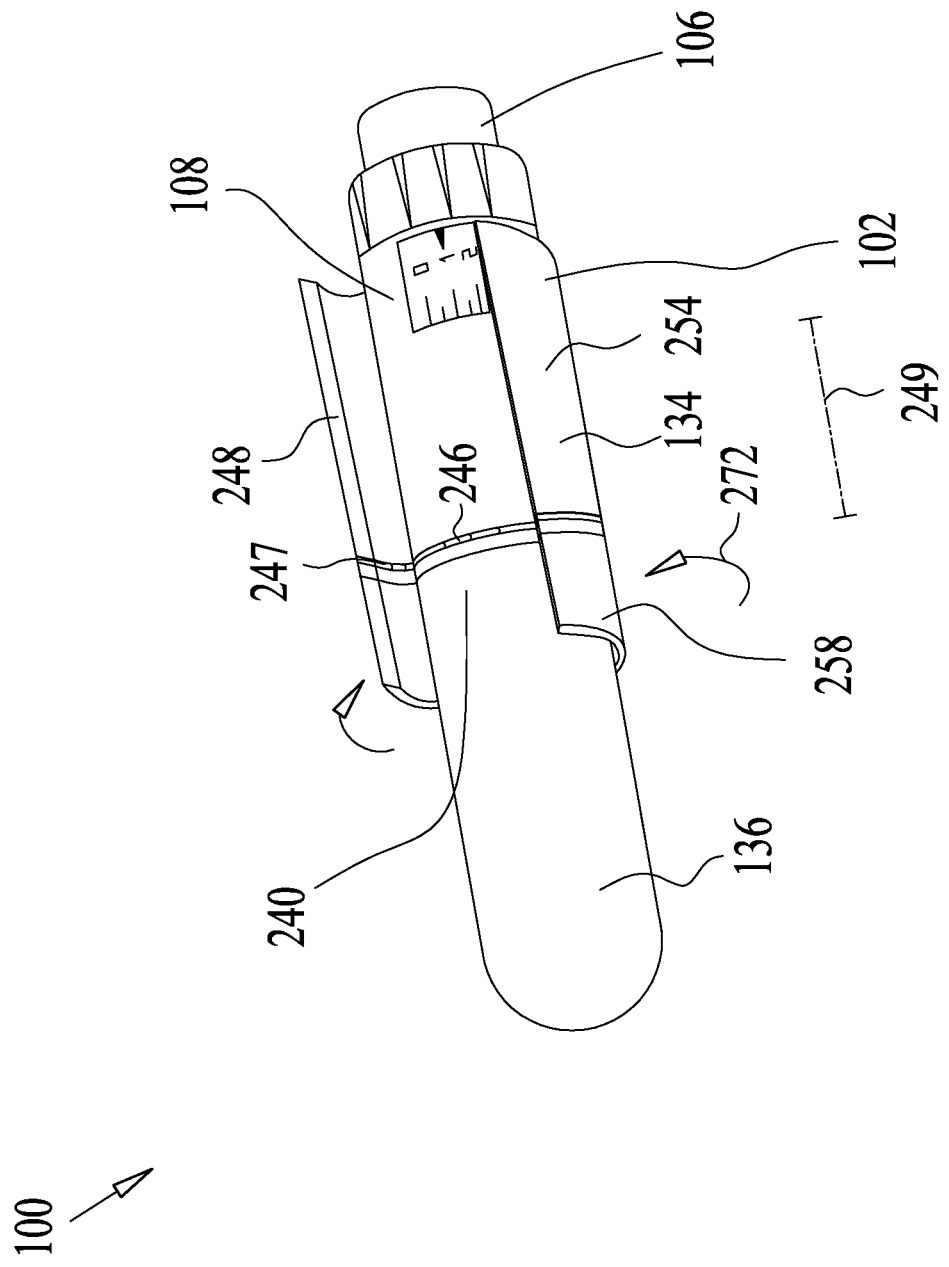
FIGS. 22A, 22B and 22C are schematic illustrations of an exemplary drug dispensing-tracking system according to some embodiments of the present disclosure, at a disassembled state (22A), at a first assembled operational state (22B) and at a second assembled operational state (22C), respectively.

In some embodiments, injection device 106 may be configured with the mechanical feature, which may comprise, for example, any structural feature, or the shape of the injection device 106 or a feature thereof. The structural feature may include a topographical feature on an external surface 240 (FIG. 22A) of the injection device 106. The topographical feature may comprise for example, a protrusion, a dent, a notch, a recess or an aperture and may be formed in any location of the injection device 106. In some embodiments, the sleeve 134 may be formed with a mechanical feature configured to correspond with the mechanical feature of the injection device 106. In a non-limiting example as shown in FIG. 22A, the injection device 106 may be formed with a circumferential recess 246 in proximity to the interface between the cap 136 and shaft 108. The sleeve 134 may be formed with a corresponding circumferential protrusion 247 and may fit within the circumferential recess 246.

The mechanical feature of the injection device 106 may comprise any feature allowing the sleeve to connect thereto. For example, the mechanical feature may comprise a relevant dimension, such as a predetermined circumference. Accordingly, the sleeve 134 may be formed with a corresponding circumference for fitting the injection device 106.

In some embodiments, commercial injection devices are designed by each manufacturer usually with unique mechanical features. According to some embodiments, the sleeve 134 may be formed with mechanical features corresponding to the unique mechanical features of a selected commercial injection device and may be non-interchangeable with another sleeve formed with mechanical features corresponding to the unique mechanical features of another selected commercial injection device. Accordingly, each sleeve may be identified by its mechanical features and may be associated with a selected commercial injection device. Each type of a commercial injection device 106 may be configured to inject a specific type of drug and a specific dose. Therefore, in identifying the corresponding sleeve, the specific type of drug and a specific dose may also be identified.

In some embodiments, the sleeve 134 may comprise a longitudinal perforation or opening 248 along the longitudinal axis 139 (FIG. 10) on at least a portion thereof. The sleeve 134 may be mounted on the tracking device 102 by opening the sleeve 134 at its perforation 248 (FIG. 22A), placing the injection device 106 within the sleeve 134 and closing the sleeve 134 over the injection device 106 (FIG. 22B).

In some embodiments, the sleeve 134 may be formed with an attachment feature for connecting to the injection device 106, such as a threaded attachment, an O-ring, a cord, a sealant, or any other attachment feature securing the tracking device 102 to the injection device 106.

Figure 22B:
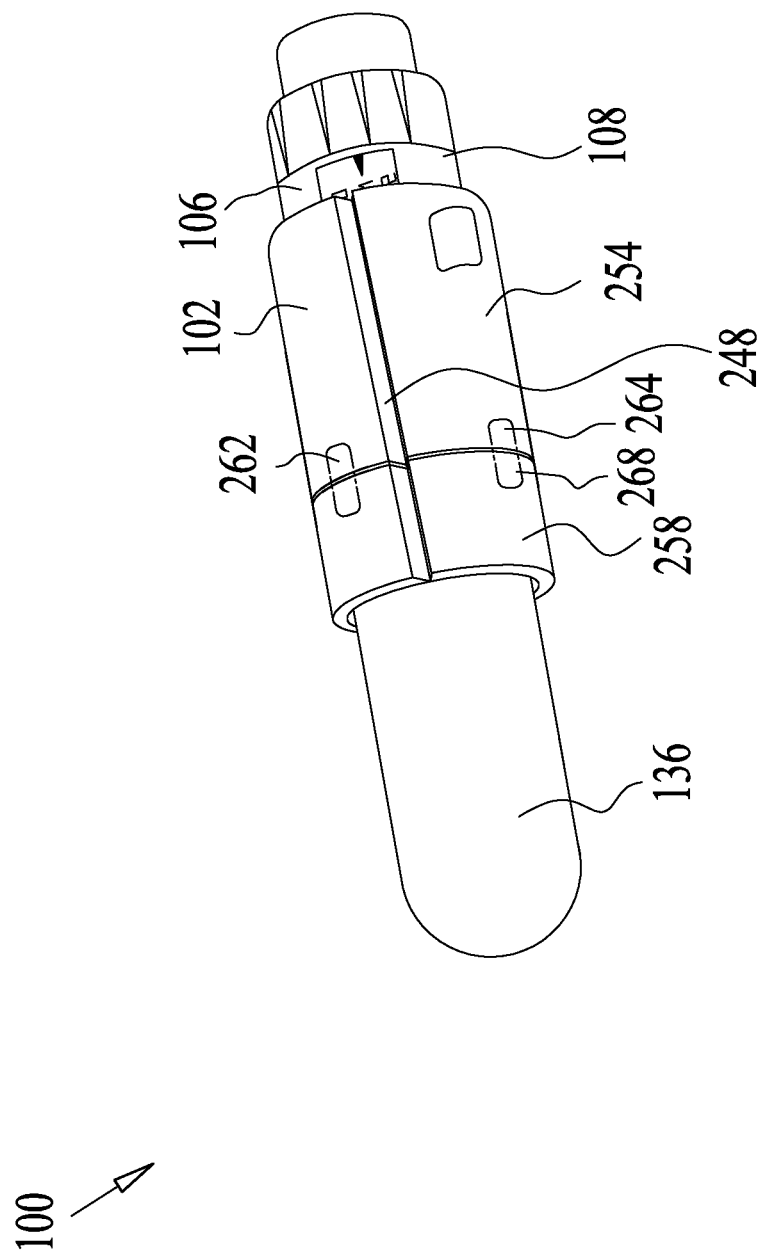

FIGS. 22A-23 are illustrations of an exemplary drug dispensing-tracking system 100. As shown, a tracking device 102 may be formed with a first section 254 inserted on the shaft 108 and a second section 258 inserted on the cap 136. A mechanical connection, such as at least one pin 262 (FIG. 22B-23) may connect the first section 254 to the second section 258. The pins 262 may be configured to separate into two first and second portions 264 and 268, each placed on the corresponding first section 254 and the second section 258.

In some embodiments, as seen in FIG. 22A, the sleeve 134 comprises mechanical features including the perforation 248, and can be opened along its longitudinal axis 249. Mounting the sleeve 134 on the injection device 106 may be performed when the cap 136 of the injection device 106 is mounted properly on the injection device 106. Opening the sleeve 134 along its longitudinal axis 249, fits its mechanical features to the injection device mechanical features, while the perforation 248 of the sleeve 134 is next to the area of the injection device 106 between the cap 136 and the body (e.g. the shaft 108) of the injection device 106. Closing the sleeve 134 in the orientation of arrow 272, may fix the perforation 248 where the cap 136 and body of the injection device connect, such that disconnecting the cap 136 from the injection device 106 breaks the perforation of the sleeve 134, leaving first section 254 firmly affixed to the body of the injection device and second section 258 firmly affixed to the cap 136 of the injection device, as shown in FIG. 22C.

Figure 22C:
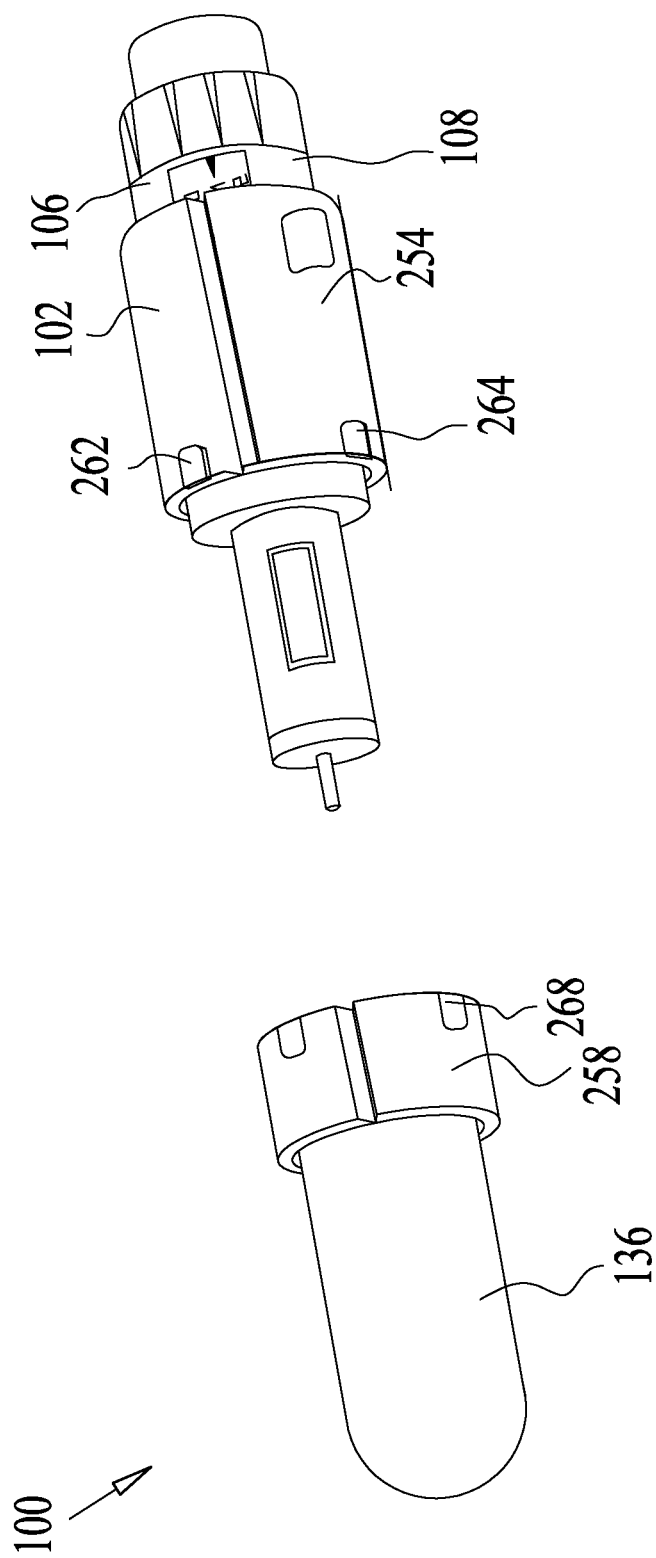

Turning to FIGS. 22B and 22C, upon removal of the cap 136 from the injection device 106, such as prior to operating the injection device 106, the first pin portion 264 disconnects from the second portion 268. The tracking device 102 is formed such that the disconnection of the pin portions 264 from 268 triggers the sensor 140 to commence its detecting operation. Upon reinserting the cap 136 on the injection device 106 and hence reconnecting the first pin portion 264 to the second pin portion 268, the sensor operation may be terminated.

In some embodiments, the pin 262 may comprise an activation pin configured to turn on the switch 228 (FIG. 2) upon disconnection of the first portion 264 from the second portion 268 via appropriate electrical circuitry and components.

As seen in FIG. 22B, the first and second portions 264 and 268 may be connected and the sensor has yet to commence its operation. Upon removal of cap 136, the first and second portions 264 and 268 are disconnected, as seen in FIGS. 22C and 23, thereby triggering the detection operation, which may operate as described in reference to FIGS. 1-20. In this embodiment, the operating of the tracking device 102 is switched on or off in a simple manner due to the simple, mechanical operation of the pins 262.

In some embodiments, the tracking device 102 may be configured to be used with a single (disposable or multiple use) injection device 106. In some embodiments the tracking device 102 may be configured for multiple use and may be placed on a plurality of injection devices 106.

Figure 24:
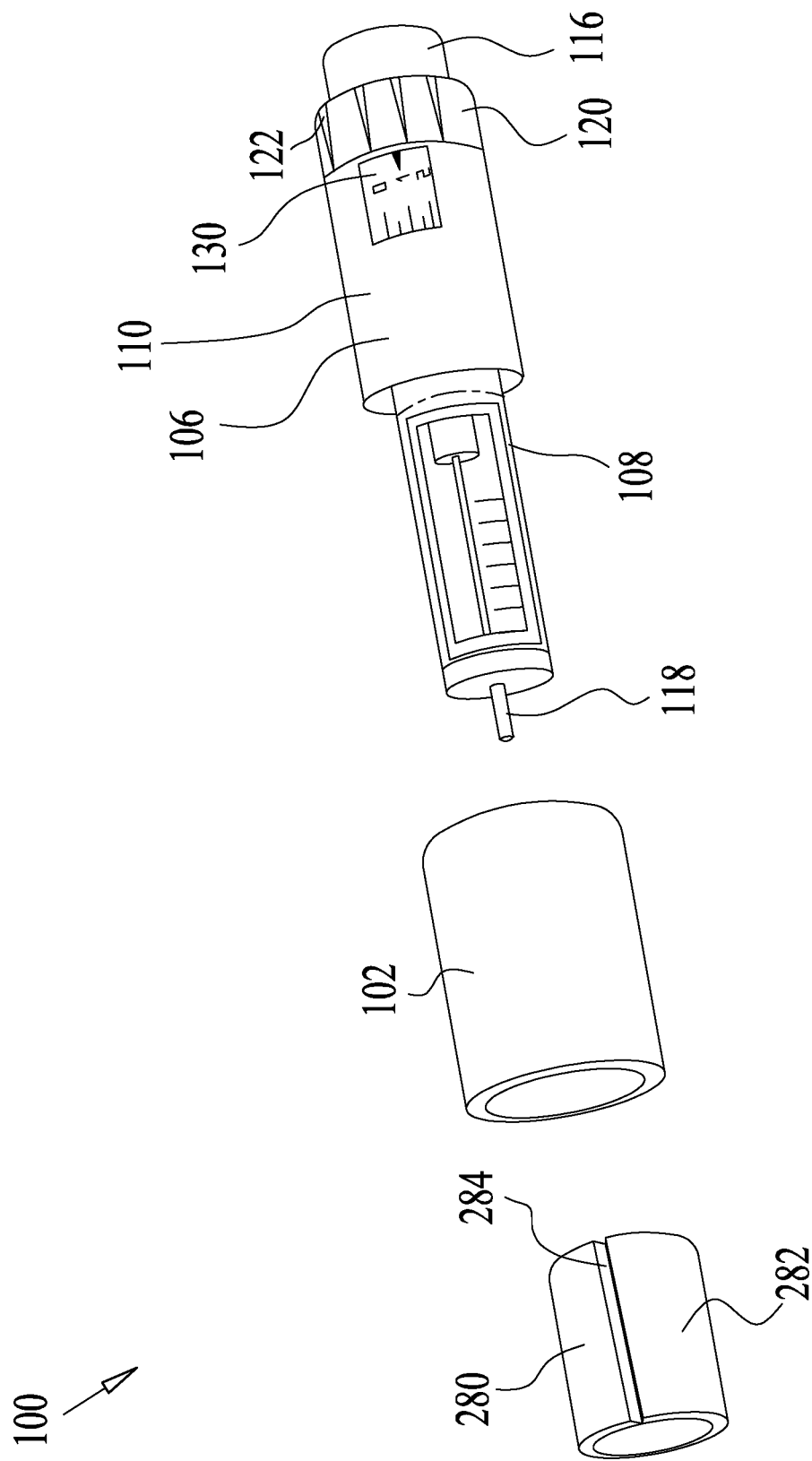
FIG. 24 is a schematic illustration of an exemplary drug dispensing-tracking system according to some embodiments of the present disclosure.

In some embodiments, as seen in FIG. 24, an adapter 280 may be configured to fit the sleeve 134 or cap 148 with various sized injection devices 106. The adapter 280 may be formed in any suitable configuration, such as a ring 282 formed of a flexible material. The ring 282 may be formed with a slit 284 to allow the ring to fit various sized injection devices 106. The ring 282 may be formed for insertion of the sleeve 134 or cap 148 thereon.

Figure 25:
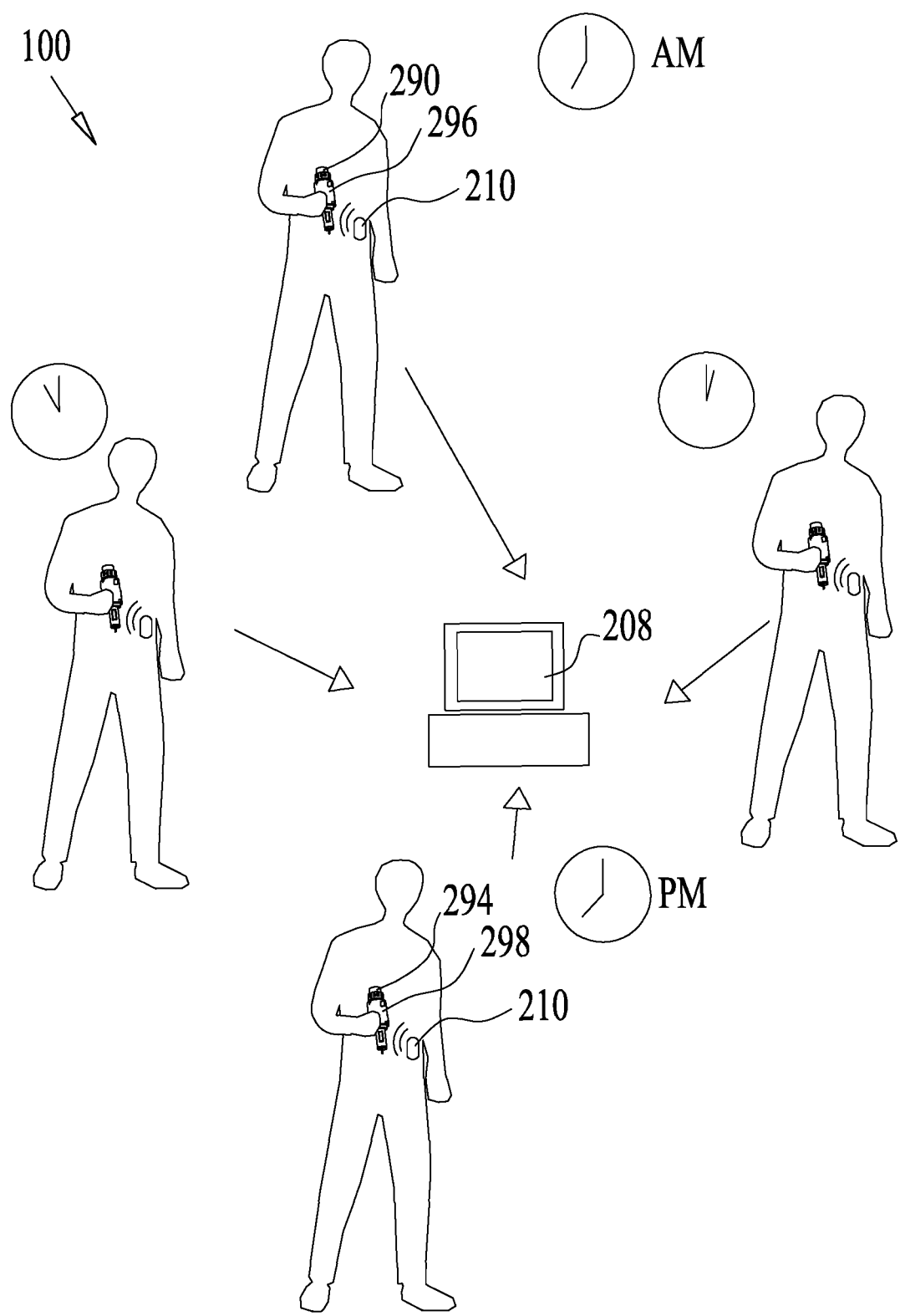
FIG. 25 is a schematic illustration of an exemplary drug dispensing-tracking system according to some embodiments of the present disclosure.

FIG. 25 is a schematic illustration of an exemplary drug dispensing-tracking system 100 according to some embodiments. As seen in FIG. 25, a user may use different injection devices during the treatment course, such as a first injection device 290 in the morning and a second injection device 294 at night.

Each injection device 106 may be designed with different mechanical, electrical and/or pharmaceutical features, as common in the commercial injection device market. Accordingly, the tracking devices 102 may be configured to fit the features of the different injection devices. For example, the injection device 106 may be formed with unique mechanical features and the tracking device 102 may be formed with corresponding mechanical features, as shown for example in FIGS. 22A-23. In some embodiments, the adaptor 280 (FIG. 24) may be used to fit the tracking device 102 with the injection device 106.

As described above, as each commercial injection device 106 may be configured to inject a selected drug and a selected dose, identifying the corresponding sleeve may also identify the selected drug and a selected dose. This identifying information may be transmitted to the external unit 204 and/or central database 208.

Similarly, the sensor 140 of a first tracking device 296 may be calibrated to detect an injection of a first drug or dosage by the first injection device 290. A sensor 140 of a second tracking device 298 may be calibrated to detect an injection of a second drug or dosage by the second injection device 294.

Each injection device 290 or 294 may include a unique identifier and the unique identification may be transmitted to the external unit 204, here shown as the treatment device 210.

In some embodiments, the carrier frequency of the signal from the sensor 140 may be utilized as the unique identifier of a specific type of injection device 106. The external unit 204 may include electronics with several electronic filters, at least some used to detect signals broadcasted from a different injection devices 106, allowing the external unit 204 to analyze signals from different injection device 106 and record the dose of drug injected from each one of them along with time and date information or any other relevant data.

The data from the different tracking devices 296 and 298 may be transmitted via the external unit 204 (or directly) to the central database 208. Thus, in some embodiments, systems, methods and devices may collect, store and log data from a plurality of injection events and/or injection devices, which, without the tracking device according to some embodiments, would be lost.

FIG. 26 is a graph illustrating a method for tracking the injection of a drug from the injection device 106 according to some embodiments. FIG. 26 shows an injection event where a microphone was used to track the rotations of the knob 120. The total detected rotations in the first direction (e.g. clockwise) is 8 (shown as the downwardly oriented signals 300) and the total detected rotations in the opposite direction (e.g. counterclockwise) is 2 (shown as the upwardly oriented signals 310). The sum of the rotations may be counted, representing the dose of drug to be injected. In a non-limiting example, rotation in the first direction indicates adding a predetermined drug dose unit "X" and rotation in the second, opposite direction indicates subtracting the predetermined drug dose unit "X". Accordingly, the data logged on the central database 208 can indicate that the total dose of the injected drug is 8X−2X=6X units.

Various implementations of some of embodiments disclosed, in particular at least some of the processes discussed (or portions thereof), may be realized in digital electronic circuitry, integrated circuitry, specially configured ASICs (application specific integrated circuits), computer hardware, firmware, software, and/or combinations thereof. These various implementations, such as associated with the drug dispensing-tracking system 100 and the components thereof, for example, may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions/code for a programmable processor, for example, and may be implemented in a high-level procedural and/or object-oriented programming language, and/or in assembly/machine language. As used herein, the term "machine-readable medium" refers to any computer program product, apparatus and/or device (e.g., non-transitory mediums including, for example, magnetic discs, optical disks, flash memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a LCD (liquid crystal display) monitor and the like) for displaying information to the user and a keyboard and/or a pointing device (e.g., a mouse or a trackball, touchscreen) by which the user may provide input to the computer. For example, this program can be stored, executed and operated by the dispensing unit, remote control, PC, laptop, smartphone, media player or personal data assistant ("PDA"). Other kinds of devices may be used to provide for interaction with a user as well. For example, feedback provided to the user may be any form of sensory feedback (e.g., visual feedback, auditory feedback, or tactile feedback), and input from the user may be received in any form, including acoustic, speech, or tactile input. Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components.

The components of the system may be interconnected by any form or medium of digital data communication (e.g., a communication network). Examples of communication networks include a local area network ("LAN"), a wide area network ("WAN"), and the Internet. The computing system according to some such embodiments described above may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented anywhere in the present application, are herein incorporated by reference in their entirety.

Example embodiments of the devices, systems and methods have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements/features from any other disclosed methods, systems, and devices, including any and all features corresponding to translocation control. In other words, features from one and/or another disclosed embodiment may be interchangeable with features from other disclosed embodiments, which, in turn, correspond to yet other embodiments. Furthermore, one or more features/elements of disclosed embodiments may be removed and still result in patentable subject matter (and thus, resulting in yet more embodiments of the subject disclosure).

What is claimed is:

1. A drug tracking device configured in the form of at least one of a cover, a sleeve, and a cap, and configured to connect with a drug-injection device, the drug-tracking device comprising:
   at least one or more of: an acoustic sensor and a vibration sensor;
   an optical sensor;
   the at least one acoustic sensor or vibration sensor being configured to produce at least one respective signal in response to sensing a vibration or a sound, produced by the drug-injection device due to an activity of the drug-injection device;
   the at least one optical sensor being configured to produce at least one respective signal in response to sensing light, produced by the drug-injection device due to an activity of the drug-injection device;
   one or more light sources configured for illuminating a predetermined location on the drug-injection device;
   one or more optical devices configured for directing light from the predetermined location to the optical sensor; and a processor having operating thereon computer instructions for causing the processor to perform at least one of: receive, transmit, analyze and/or store information, at least a portion of the information comprising the at least one respective signal, wherein the optical sensor is configured to detect an optical signal including light of a predetermined wavelength, to avoid detection of light from the ambient environment external to the drug-injection device.

2. The device of claim 1, wherein the activity comprises at least one of: setting or adjusting an amount of drug to inject, injecting the drug, and readying the drug-injection device.

3. The device of claim 1, wherein any one of the acoustic sensor, vibration sensor and optical sensor comprises a plurality of sensors and wherein the plurality of sensors are spaced apart along and/or around the drug-tracking device.

4. The device of claim 1, wherein the drug-injection device comprises the vibration sensor and a pen-injection device wherein the amount of drug to be injected is set by rotating an injection-amount knob included with the drug-injection device, wherein a series of clicking sounds and/or vibrations are produced by the rotation each of which is sensed by the vibration sensor and wherein the vibration sensor produces the at least one signal corresponding to the sensed sounds and/or vibrations.

5. The device of claim 4, wherein the drug-injection device comprises the vibration sensor and the sound and/or vibration of the rotation of the knob comprises a first sound and/or vibration for rotation of the knob in a first direction and a second sound and/or vibration in a second direction, and wherein the computer instructions are additionally configured to adjust one or more of the amount of drug injected by the drug-injection device, and/or an amount of drug remaining in a reservoir associated with the drug-injection device.

6. The device of claim 1, wherein the drug-injection device comprises the vibration sensor and a pen-injection device having an injection push-button configured to initiate injection of the drug into a patient using injection dispensing means, wherein at least one of sound(s) and/or vibrations of at least one of the pushing of the button and the dispensing means is sensed by the vibration sensor, and wherein the vibration sensor produces the at least one signal corresponding to the sensed sounds and/or vibrations.

7. The device of claim 1, further comprising a transceiver for at least one of transmitting and receiving information to/from a wireless device.

8. The device of claim 1, wherein the drug-tracking device is configured as a cap to fit over the drug-injection device.

9. The device of claim 8, wherein an amount of drug to be injected is set by rotating an injection-amount knob included with the drug-injection device and wherein the drug-injection device comprises an injection push-button configured to initiate injection of the drug into a patient using injection dispensing means; and wherein the cap is configured such that any one of the acoustic sensor, vibration sensor and optical sensor are arranged thereon to be proximate the knob and/or push-button when the cap is mounted on the drug-injection device.

10. The device of claim 1, wherein the drug-injection device includes a shaft, and wherein the drug-tracking device is configured as a sleeve and the sleeve is configured to be received onto the shaft.

11. The device of claim 1, wherein at least a portion of the drug-tracking device includes a coupling material configured to relay a sound(s) and/or vibration.

12. The device of claim 1, wherein at least a portion of the drug-tracking device includes an isolating material configured to isolate sounds not generated by the drug-injection device.

13. The device of claim 1, wherein the optical sensor is selected from the group consisting of: CCD, a CCD array, a photodiode, a waveguide, and a combination of any of the foregoing.

14. The device of claim 1, wherein the one or more optical devices are selected from the group consisting of one or more: lenses, light-guides, and beam splitters.

15. The device of claim 1, wherein the predetermined wavelength comprises an invisible wavelength.

16. The device of claim 1, wherein the processor is configured to compare an image captured by the optical sensor to a previous image captured by the optical sensor.

17. The device of claim 1, wherein the drug-injection device comprises the vibration sensor and the optical sensor is initially inactive and the vibration sensor is configured to prompt the commencement of the operation of the dormant optical sensor.

18. The device of claim 1, and including an adaptor configured to fit the drug-tracking device with various sized drug-injection devices.

19. The device of claim 18, wherein the adaptor comprises a flexible material.

* * * * *